US009671366B2

(12) United States Patent
Orwar et al.

(10) Patent No.: US 9,671,366 B2
(45) Date of Patent: *Jun. 6, 2017

(54) PIPETTES, METHODS OF USE, AND METHODS OF STIMULATING AN OBJECT OF INTEREST

(71) Applicant: Fluicell AB, Göteborg (SE)

(72) Inventors: Owe Orwar, Hovås (SE); Alar Ainla, Somerville, MA (US); Aldo Jesorka, Göteborg (SE)

(73) Assignee: Fluicell AB, Göteborg (SE)

(*) Notice: Subject to any disclaimer, the term of this patent is extended or adjusted under 35 U.S.C. 154(b) by 0 days.

This patent is subject to a terminal disclaimer.

(21) Appl. No.: 14/823,199

(22) Filed: Aug. 11, 2015

(65) Prior Publication Data

US 2015/0346147 A1 Dec. 3, 2015

Related U.S. Application Data

(63) Continuation of application No. 13/486,599, filed on Jun. 1, 2012, now Pat. No. 9,126,197, which is a continuation of application No. PCT/IB2010/003307, filed on Dec. 3, 2010.

(60) Provisional application No. 61/266,255, filed on Dec. 3, 2009.

(51) Int. Cl.
*G01N 27/447* (2006.01)
*B01L 3/02* (2006.01)
*B01L 3/00* (2006.01)
*G01N 33/487* (2006.01)

(52) U.S. Cl.
CPC ........ *G01N 27/44743* (2013.01); *B01L 3/022* (2013.01); *B01L 3/5027* (2013.01); *B01L 3/502715* (2013.01); *G01N 27/44791* (2013.01); *G01N 33/48728* (2013.01); *B01L 3/50273* (2013.01); *B01L 2200/06* (2013.01); *B01L 2200/0694* (2013.01); *B01L 2300/0645* (2013.01); *B01L 2300/0877* (2013.01); *B01L 2400/0415* (2013.01); *B01L 2400/0487* (2013.01); *Y10T 436/25* (2015.01)

(58) Field of Classification Search
CPC ....... G01N 27/44743; G01N 27/44791; G01N 33/48728; B01L 3/022; B01L 3/5027; B01L 3/502715; B01L 3/50273; B01L 2200/06; B01L 2200/0694; B01L 2300/0877; B01L 2400/0415; B01L 2400/0487; Y10T 436/25
See application file for complete search history.

(56) References Cited

U.S. PATENT DOCUMENTS

| 5,726,404 A | 3/1998 | Brody |
| 7,314,595 B2 | 1/2008 | Honkanen et al. |
| 7,740,472 B2 | 6/2010 | Delamarche et al. |
| 2005/0247673 A1 | 11/2005 | Delamarche et al. |
| 2006/0127579 A1 | 6/2006 | Delamarche et al. |
| 2006/0234298 A1* | 10/2006 | Chiu .................. B01L 3/5025 435/7.1 |
| 2007/0231458 A1 | 10/2007 | Gale et al. |

FOREIGN PATENT DOCUMENTS

| EP | 1366820 A1 | 12/2003 |
| WO | WO 03/068906 A1 | 8/2003 |
| WO | WO 2004034185 A2 | 4/2004 |
| WO | WO 2010128483 A2 | 11/2010 |

OTHER PUBLICATIONS

Ainla, A., et al., 2010, "A Microfluidic Pipette for Single-Cell Pharmacology", Anal. Chem. 82, 4529-4536.
Chen, D., et al., 2008, "The chemistrode: A droplet-based microfluidic device for stimulation and recording with high temporal, spatial, and chemical resolution", PNAS, 105(44), 16843-16848.
Feinerman, O., et al., 2003, "A picoliter 'fountain-pen' using co-axial dual pipettes", Journal of Neuroscience Methods, 127, 75-84.
Juncker, D., et al., 2005, "Multipurpose microfluidic probe", Nature Materials, 4, 622-628.
Lovchik, R. D., et al., 2009, "Multilayered microfluidic probe heads", J. Micromech. Microeng. 19, 1-8.
Queval, A., et al., 2010, "Chamber and microfluidic probe for microperfusion of organotypic brain slices", Lab Chip, 10, 326-334.
International Search Report, PCT/IB2010/003307, Sep. 27, 2011.
Written Opinion of the International Searching Authority, PCT/IB2010/003307, Jun. 3, 2012.
International Preliminary Report on Patentability, PCT/IB2010/003307, Jun. 5, 2012.
Extended European Search Report, European Patent Application No. 15199422.5, Mar. 8, 2016.
European Application No. 10 821 464.4, Communication pursuant to Article 93(3) EPC (Sep. 10, 2015).

* cited by examiner

*Primary Examiner* — Andrea S Grossman
(74) *Attorney, Agent, or Firm* — Saul Ewing LLP; Brian R. Landry

(57) ABSTRACT

One embodiment of the invention provides a system adapted and configured to generate a localized flow circulation zone. The system includes: a free-standing microfluidic pipette comprising three or more channels with exits separated from each other by an outer surface of the pipette; and a controller programmed to control fluid flows through each of the three or more channels to generate a localized recirculating fluid flow path outside the pipette. Liquid leaving the microfluidic pipette through at least one outlet channel exit is withdrawn through at least two inlet channel exits.

20 Claims, 28 Drawing Sheets

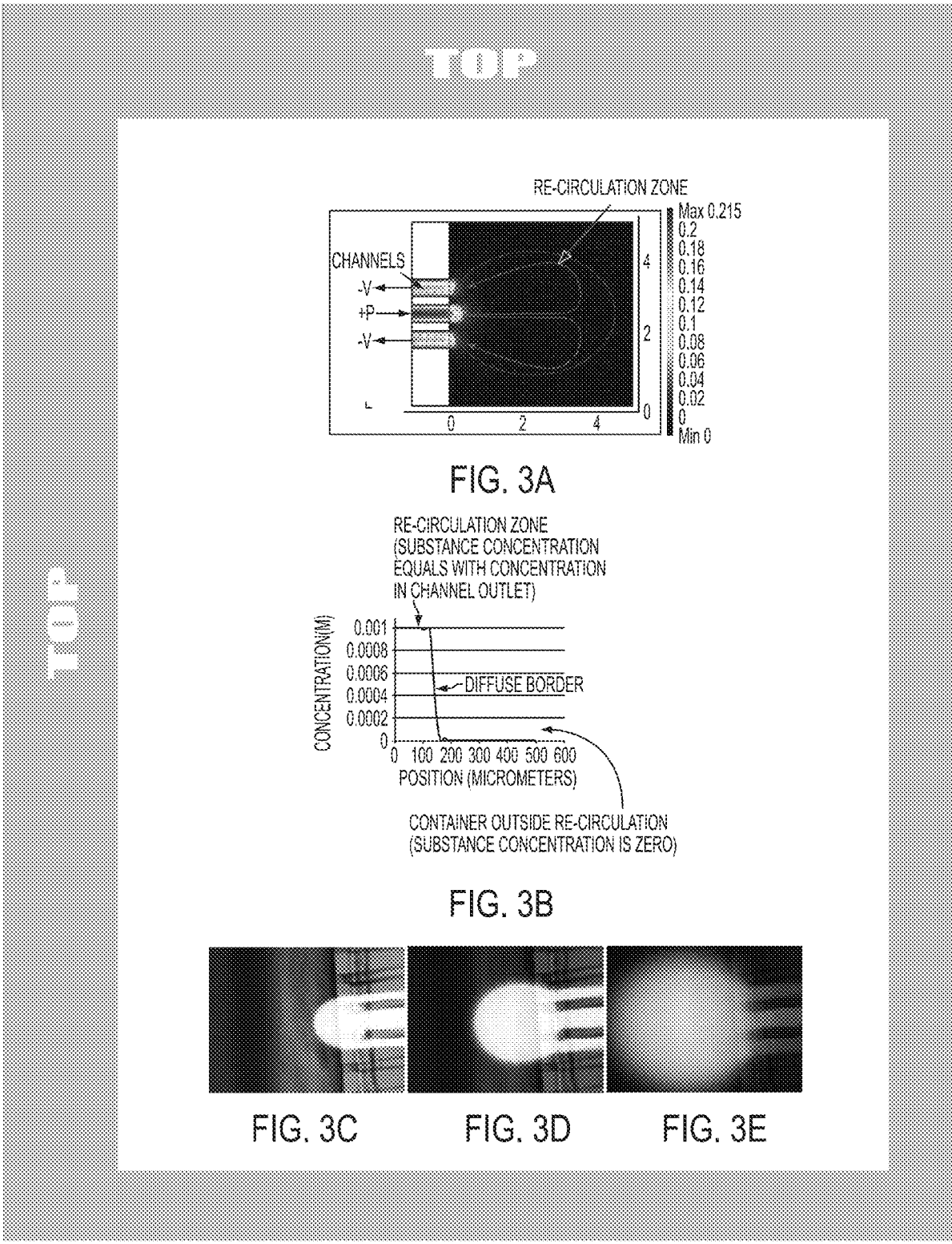

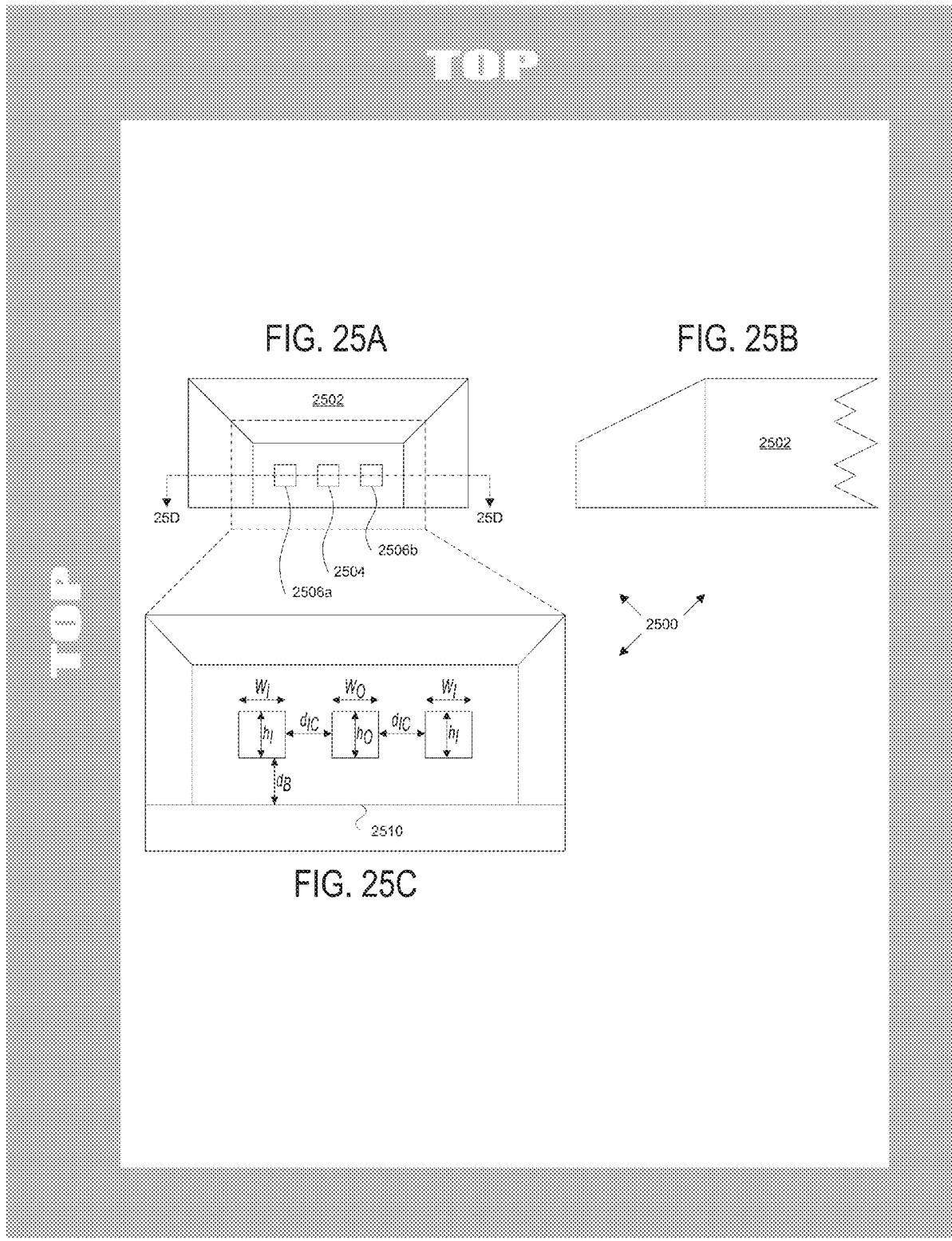

PIPETTES, METHODS OF USE, AND METHODS OF STIMULATING AN OBJECT OF INTEREST

CROSS-REFERENCE TO RELATED APPLICATION

This application is a continuation under 35 U.S.C. §120 of U.S. patent application Ser. No. 13/486,599, filed Jun. 1, 2012, which is a continuation under 35 U.S.C. §120 of International Application No. PCT/IB2010/003307, filed Dec. 3, 2010, which claims priority to U.S. Provisional Patent Application No. 61/266,255, filed Dec. 3, 2009. The entire contents of each of these applications is hereby incorporated herein by reference.

BACKGROUND OF THE INVENTION

Since their invention, glass micropipettes have been indispensable tools for molecular and cellular biologists. They can be used for microinjection to mechanically penetrate the cell's membrane and inject or sample material to and from the cell's interior. Examples include transplanting the nucleus, making molecular cloning possible. Micropipettes can also be used to make electrical contact to the cell interior, which is the foundation of the patch-clamp technique.

Glass micropipettes are suited for establishing a mechanical contact with a single cell by penetrating through the lipid membrane. However, penetration may often be unfavorable, since it can destroy or deteriorate the internal structure of the cell and affect its normal physiology. Thus, in many experiments it is favorable to communicate with the cells in the same way nature does—by external chemical stimulation. However, conventional glass pipettes are difficult to use in order to establish a non-mechanical, purely chemical contact with a microscopic object. For example, if exposure of the cell to a chemical stimulus is desired, a conventional micropipette can be used to inject the active substrate to the vicinity of the cell. To maintain constant concentration, such an injection must be continuous; otherwise the concentration will decrease rapidly by diffusion. The constant injection on the other hand will cause accumulation of active substrate outside of the microscopic experimental region, which contaminates other cells or surfaces and severely limits further studies in the same system.

Therefore, there is a need in the art for a device that is capable of suitably controlling the chemical environment in the microscopic region around the cell or around an artificial sensor element, without cross-contaminating other cells in the culture or other elements fabricated on the same surface.

Further, many experiments require that the object of interest is exposed to a programmed sequence of chemical stimuli, with well-controlled temporal resolution. This can be achieved by different superfusion techniques, which can be based on different glass tubes, for example, the θ-tube or multi-barrel systems, where solution exchange times can be as short as 200-400 μs. However, these devices may result in cross-contamination and do not allow spatial concentration control with high precision.

Accordingly, to address such high-resolution spatial concentration control, microfluidics systems can preferably be used. However, conventional microfluidic devices lack an important capability of a pipette, which is the control of position relative to the macroscopic reservoir, or open volume. Instead, the microscopic sensor (for example, but not only limited to, a single cell) must be scanned in front of the channel array for superfusion. This considerably restricts the applicability of the superfusion device and makes it considerably more difficult to expose an arbitrary region such as a cell, microfabricated structures, sensors, and/or actuators attached on a surface, a single cell in a large cell culture or tissue, extended structures built on a surface (e.g., lipid-nanotube networks), and micro/nanofabricated objects on a surface.

Further, some experiments require the exposure of microscopic objects to precisely defined chemical gradients. For example, studies of chemotaxis are important for the understanding of embryogenesis, cancer metastasis, cell growth, and tissue formation. Stable microscopic chemical gradients are difficult to achieve with macroscopic tools. Currently, microfluidics have been employed for these studies. However, cell handling in microfluidic devices is not trivial and it is highly desirable to generate chemical gradients on arbitrary areas in an open reservoir, where an object of interest is located, either as a single sensor or within a collective of sensors.

In addition, various mechanical and practical problems may be associated with glass pipettes, such as backfilling, breaking upon accidental contact with surfaces or objects, damage to cells and tissue, adsorption of chemical agents or biological matter to the glass surface, the need for specialized pulling equipment, and the need for a specifically designed needle holder.

Accordingly, there remains a need in the art for improved microfluidic pipettes.

SUMMARY OF THE INVENTION

The present invention provides a pipette having solution exchange and fluid recirculation capabilities, and methods for using the pipette.

In particular, the invention provides a free-standing pipette with both solution exchange capability and fluid recirculation into a functional microflow pipette, enabling highly localized and contamination-free fluid delivery within a closely confined volume in the vicinity of the pipette outlet. Preferably, the device allows direct translational positioning, so the pipette can be suitably directed at a point of interest at any desired angle, such as a biological or artificial cell, a defined surface area or a sensor element, using micro- or nanopositioning techniques.

In a first aspect, the invention features a free-standing pipette, comprising a microfluidic device comprising one or more channels with exits leading into an open-volume.

In one embodiment, the pipette is tapered at one end.

In another aspect, the invention also features a free-standing tapered pipette, comprising a microfluidic solution exchange device, which has one channel exit or several side-by-side channel exits leading into an open-volume near or at its tapered end, where the smallest dimension of the tapered end is in the sub-millimeter size range.

In another aspect, the invention features a free-standing microfluidics solution exchange pipette, comprising a microfluidic device, which has one channel exit or several side-by-side channel exits leading into a liquid open-volume, where the open-volume container is independent from the microfluidic device, and flow circulation, where the outflow of one or more channels is circulating fully or partially back into the microfluidics device via one or more channels.

In another embodiment, the tapered end is between 1-1000 μm. In another embodiment, the tapered end is between 1-500 µm. In another further embodiment, the tapered end is between 1-100 µm in width.

In another embodiment, the two or more channel exits are side by side channel exits.

In another further embodiment, the two or more channel exits are arranged in a one dimensional array.

In another embodiment, the three or more channel exits are arranged in a two-dimensional array.

In a further embodiment, the one or more channel exits lead into an open volume near or at the tapered end.

In one embodiment, the open volume is separate from the microfluidic device.

In another embodiment, the open volume comprises a fluid filled container.

In another further embodiment, the open volume comprises a droplet on a surface.

In a further embodiment, the open volume comprises a suspended droplet.

In one embodiment, the free-standing pipette further comprises a positioning device.

In another embodiment, the positioning device is micromanipulators.

In a further embodiment, the positioning device and the microfluidic device are attached, and the positioning device enables alignment of the channel exits of the microfluidic device to an object of interest in the open volume on the surface.

In another embodiment, the object of interest is selected from sensors, cells and surface embedded elements or combinations thereof.

In another further embodiment, the channel exits have a circular cross-section.

In one embodiment, the channel exits have a rectangular cross-section.

In another embodiment, the channel exits have a semi-circular cross-section.

In another embodiment, the device is mechanically bent to enhance vibration stability.

In another embodiment, the channel exit plane is perpendicular to the device bottom plane.

In still a further embodiment, the channel exit plane is not perpendicular to the device bottom plane.

In one embodiment, the pipette consists fully or partially of one or more elastic polymers.

In another embodiment, the pipette consists fully or partially of one or more non-elastic polymers.

In another further embodiment, the pipette consists fully or partially of glass, ceramics or metal.

In still another embodiment, the free-standing pipette further comprises flow circulation through the one or more channels.

In another embodiment, the flow circulation is simultaneous flow circulation.

In a further embodiment, the flow circulation is sequential flow circulation.

In one embodiment, the flow circulation is a combination of simultaneous and sequential flow circulation.

In another embodiment, the outflow of one or more channels circulates back into the microfluidics device via a channel. In one embodiment, the channel that provides for circulation back into the device is under negative pressure and/or a vacuum or is subject to an electric field.

In still a further embodiment, flow circulation is driven by hydrostatic pressure.

In one embodiment, flow circulation is driven by pneumatic pressure.

In one embodiment, flow circulation is driven by an electric field.

In one embodiment, flow circulation is driven by an integrated device.

In another embodiment, the integrated device is a pump.

In another embodiment, the free-standing pipette comprises one channel with an exit that is switched between an outlet and an inlet to create a recirculation zone.

In another embodiment, the distance from an edge of the channel exits to a bottom surface of the microfluidic device is between about 0.5 to 2 times the vertical height of the channels.

In another embodiment, the distance from an edge of the channel exits to a bottom surface of the microfluidic device can be between about 10 µm and about 20 µm.

In another embodiment, the distance from an edge of the channel exits to a bottom surface of the microfluidic device can be less than about five times the vertical height of the channels.

In another embodiment, the distance from an edge of the channel exits to a bottom surface of the microfluidic device can be less than about twice the vertical height of the channels.

In another embodiment, the distance from an edge of the channel exits to a bottom surface of the microfluidic device can be less than the vertical height of the channels.

The invention also features a method of solution exchange comprising: providing a free-standing pipette, the free-standing pipette including a microfluidic device comprising one or more channels with exits leading into an open-volume; and causing flow circulation through the one or more channels, wherein flow exiting the one or more channels circulates back into the microfluidic device.

In one embodiment, the solution exchange is within a recirculation zone.

In one embodiment, the flow circulation is simultaneous flow circulation.

In another embodiment, the flow circulation is sequential flow circulation.

In another embodiment, the flow circulation is a combination of simultaneous and sequential flow circulation.

In another embodiment, the outflow of one or more channels circulates back into the microfluidics device.

In one embodiment, flow circulation is driven by hydrostatic pressure.

In one embodiment, flow circulation is driven by pneumatic pressure.

In one embodiment, flow circulation is driven by an electric field.

In one embodiment, flow circulation is driven by an integrated device.

In one embodiment, the integrated device is a pump.

In one embodiment, solution-exchange within the recirculation zone occurs in an open volume and the recirculation zone does not reach any boundary of the open volume.

In a further embodiment, solution-exchange within the recirculation zone occurs in an open volume and the recirculation zone reaches one or more boundaries of the open volume.

In one embodiment, solution-exchange within the recirculation zone occurs in an open volume and the device is in physical contact with one or more boundaries of the open volume.

In another embodiment, solution exchange is applied to cells.

In another embodiment, solution exchange is applied to chemical or biochemical sensors within the open volume.

In one embodiment, solution exchange is applied to biological sensors within the open volume.

In a further embodiment, solution exchange is applied to cells, chemical, biological, or biochemical sensors located on patterned surfaces within the open volume.

In one embodiment, solution exchange is applied to biological cells, chemical, biological, or biochemical sensors located on microelectrode surfaces within the open volume.

In another embodiment, solution exchange is applied to cells in an electrophysiology measurement environment.

In another embodiment, solution exchange is simultaneously or sequentially applied to single instances of cells, chemical, biological, or biochemical sensors within the open volume.

In another embodiment, solution exchange is simultaneously applied to two or more of biological cells, chemical, biological, or biochemical sensors within the open volume.

In still another embodiment, the recirculation zone is applied in combination with electroporation of biological or artificial cells in order to manipulate their interior volume.

In one embodiment, solution exchange within a recirculation zone is applied to two-dimensional films on surfaces within the open volume.

In one embodiment, the recirculation zone is applied to stimulate a biological cell and simultaneously transport products of the cell response into the pipette.

In another embodiment, the recirculation zone is applied to objects of interest, acting as a chemical or biochemical signal source for pulsed or continuous stimulation.

In another embodiment, the recirculation zone is applied to objects of interest, acting as a fluid sample collection device.

In a further embodiment, the recirculation zone is applied to objects of interest, acting as a chemical or biochemical signal source for pulsed or continuous stimulation and simultaneously a fluid sample collection device.

In another further embodiment, the composition of the recirculation zone is changed over time by temporal gradients of single flow constituents, temporal gradients of multiple flow constituents, or switching between different fluids or solutions.

In a further embodiment the recirculation zone is applied to a network of cells.

In yet another embodiment the network of cells is a biological tissue culture.

In an additional embodiment the network of cells is a network of neural cells.

In another further embodiment the recirculation zone is applied to cultures of single cell organisms.

In a further embodiment solution exchange is applied to cells in combination with an additional free-standing microprobe.

In yet another embodiment the additional free-standing microprobe is a glass capillary.

In an additional embodiment the additional free-standing microprobe is a microelectrode.

In another further embodiment the additional free-standing microprobe is an optical fiber.

In an embodiment of any one of the above aspects, the invention features a method of using the free-standing pipette as a directly positioned solution exchange pipette, comprising a free-standing flow circulating microfluidic pipette, which has one or more channel exits leading into an open volume, an open volume container, comprising objects of interest, and a positioning device to where the microfluidic device is attached and which enables to align the channel exits of the microfluidic device to the object of interest on the surface.

Another aspect of the invention provides a microfluidic pipette including: an optically transparent substrate defining one or more microfluidic outlet channels and one or more microfluidic inlet channels; and a dispensing region located on the exterior of substrate. Each of the one or more microfluidic outlet channels and the one or more microfluidic inlet channels include an opening on the dispensing region such that a substance dispensed from the one or more outlet channels gathers and recirculates in the dispensing regions before being withdrawn by the one or more microfluidic inlet channels.

This aspect of the invention can have a variety of embodiments. The microfluidic pipette can further include a controller programmed to control the flow of fluids within the one or more microfluidic outlet channels and the one or more microfluidic inlet channels to maintain a region of substantially constant concentration of a fluid at the dispensing region.

The microfluidic pipette can include one or more sensors in communication with the controller, the one or more sensors configured to provide data relating to the properties of a fluid at the dispensing region. The one or more sensors can include a light emission sensor. The one or more sensors can include an electrochemical sensor.

The number of microfluidic inlet channels can be greater than the number of microfluidic outlet channels. The openings of the one or more microfluidic outlet channels and the one or more microfluidic inlet channels can be arranged in a one-dimensional pattern. The openings of the one or more microfluidic outlet channels and the one or more microfluidic inlet channels can be arranged in a two-dimensional pattern.

The microfluidic pipette can include a positive pressure source in communication with the one or more microfluidic outlet channels. The positive pressure source can provide a pressure selected from the group consisting of: between about 2 kPa and about 10 kPa, between about 10 kPa and about 20 kPa, between about 20 kPa and about 30 kPa, between about 30 kPa and about 40 kPa, between about 40 kPa and about 50 kPa, between about 50 kPa and about 60 kPa, between about 60 kPa and about 70 kPa, between about 70 kPa and about 80 kPa, between about 80 kPa and about 90 kPa, and between about 90 kPa and about 100 kPa.

The microfluidic pipette can include a negative pressure source in communication with the one or more microfluidic inlet channels.

The microfluidic pipette can include a first pump in communication with the one or more microfluidic outlet channels. The microfluidic pipette can include a second pump in communication with the one or more microfluidic inlet channels.

The microfluidic pipette can include a positive electrode in communication with the one or more microfluidic outlet channels and a negative electrode in communication with the one or more microfluidic inlet channels. The controller can be further programmed to apply a voltage differential of about 100V to the positive electrode and the negative electrode.

The optically transparent substrate can be selected from the group consisting of: glass, polydimethylsiloxane (PDMS), poly(methyl methylacrylate) (PMMA), and polyethylene (PE).

The total cross-sectional area of the one or more microfluidic inlet channels can be greater than the total cross-sectional area of the one or more microfluidic outlet channels. A ratio of the total cross-sectional area of the one or more microfluidic outlet channels to the total cross-sectional area of the one or more microfluidic inlet channels can be between about 0.6:1 and about 1:1. The total cross-sectional area of the one or more microfluidic inlet channels can be substantially equal to the total cross-sectional area of the one or more microfluidic outlet channels.

The one or more microfluidic outlet channels can have a substantially square cross-section. The one or more microfluidic outlet channels can have a cross-sectional dimension selected from the group consisting of: between about 5 μm and about 10 μm, between about 10 μm and about 15 μm, between about 15 μm and about 20 μm, between about 20 μm and about 25 μm, between about 25 μm and about 30 μm, between about 30 μm and about 35 μm, between about 35 μm and about 40 μm, between about 40 μm and about 45 μm, and between about 45 μm and about 50 μm.

The one or more microfluidic outlet channels can have a substantially square cross-section. The one or more microfluidic outlet channels can have a cross-sectional dimension selected from the group consisting of: between about 5 μm and about 10 μm, between about 10 μm and about 15 μm, between about 15 μm and about 20 μm, between about 20 μm and about 25 μm, between about 25 μm and about 30 μm, between about 30 μm and about 35 μm, between about 35 μm and about 40 μm, between about 40 μm and about 45 μm, and between about 45 μm and about 50 μm.

A ratio of the distance between openings of the one or more microfluidic outlet channels and the one or more microfluidic inlet channels and a cross-sectional dimension of the one or more microfluidic outlet channels can be selected from the group consisting of: between about 0.5:1 and about 1:1, between about 1:1 and about 1.5:1, between about 1.5:1 and about 2:1, between about 2:1 and about 2.5:1, between about 2.5:1 and about 3:1, between about 3:1 and about 3.5:1, between about 3.5:1 and about 4:1, and between about 4:1 and about 4.5:1.

The one or more microfluidic outlet channels can have a length selected from the group consisting of: between about 1 cm and about 2 cm, between about 2 cm and about 3 cm, between about 3 cm and about 4 cm, between about 4 cm and about 5 cm, between about 5 cm and about 6 cm, between about 6 cm and about 7 cm, between about 7 cm and about 8 cm, between about 8 cm and about 9 cm, between about 9 cm and about 10 cm, between about 10 cm and about 11 cm, between about 11 cm and about 12 cm, between about 12 cm and about 13 cm, between about 13 cm and about 14 cm, and between about 14 cm and about 15 cm.

The one or more microfluidic outlet channels and the one or more microfluidic inlet channels can be positioned in proximity to an edge of the substrate. A ratio of the distance between openings of the one or more microfluidic outlet channels and the edge of the substrate and a cross-sectional dimension of the one or more microfluidic outlet channels can be selected from the group consisting of: between about 0.5:1 and about 1:1, between about 1:1 and about 1.5:1, between about 1.5:1 and about 2:1, between about 2:1 and about 2.5:1, between about 2.5:1 and about 3:1, between about 3:1 and about 3.5:1, between about 3.5:1 and about 4:1, and between about 4:1 and about 4.5:1. A ratio of the distance between openings of the one or more microfluidic inlet channels and the edge of the substrate and a cross-sectional dimension of the one or more microfluidic inlet channels can be selected from the group consisting of: between about 0.5:1 and about 1:1, between about 1:1 and about 1.5:1, between about 1.5:1 and about 2:1, between about 2:1 and about 2.5:1, between about 2.5:1 and about 3:1, between about 3:1 and about 3.5:1, between about 3.5:1 and about 4:1, and between about 4:1 and about 4.5:1.

A ratio of the distance between openings of the one or more microfluidic outlet channels and the edge of the substrate and a cross-sectional dimension of the one or more microfluidic outlet channels can be between about 1:1 and about 5:1. The distance between openings of the one or more microfluidic outlet channels and the edge of the substrate can be less than a cross-sectional dimension of the one or more microfluidic outlet channels.

Another aspect of the invention provides a method of stimulating an object of interest. The method includes: providing a microfluidic pipette including a substrate defining one or more microfluidic outlet channels and one or more microfluidic inlet channels; and a dispensing region located on the exterior of substrate; placing the dispensing region of the microfluidic pipette in proximity to the object of interest; causing a fluid to flow out of the one or more microfluidic outlet channels; and causing the fluid to flow into the one or more microfluidic inlet channels.

Each of the one or more microfluidic outlet channels and the one or more microfluidic inlet channels include an opening on the dispensing region such that a substance dispensed from the one or more outlet channels gathers and recirculates in the dispensing regions before being withdrawn by the one or more microfluidic inlet channels.

This aspect of the invention can have a variety of embodiments. The substrate can be optically transparent. The optically transparent substrate can be selected from the group consisting of: glass, polydimethylsiloxane (PDMS), poly (methyl methylacrylate) (PMMA), and polyethylene (PE).

The microfluidic pipette can be positioned substantially laterally with regard to the object of interest. The object of interest can be a cell.

The method can further include imaging the object of interest. The imaging step can be performed by light microscopy.

The method can further include analyzing the fluid withdrawn into the one or more inlet channels.

Another aspect of the invention provides a microfluidic pipette including: a substrate defining one or more microfluidic outlet channels, one or more microfluidic inlet channels, and a common channel in communication with the one or more microfluidic outlet channels and the one or more microfluidic inlet channel; and a dispensing region located on the exterior of the substrate and in communication with the common channel.

This aspect of the invention can have a variety of embodiments. In one embodiment, the microfluidic pipette includes a controller programmed to control the flow of fluids within the one or more microfluidic outlet channels and the one or more microfluidic inlet channels to maintain a region of substantially constant concentration of a fluid at the dispensing region. The controller can be further programmed to control the flow of fluid by alternately (i) inducing flow in the one or more microfluidic outlet channels and (ii) inducing flow in the one or more microfluidic inlet channels. The controller can be further programmed to alternate induction of flow between the one or more microfluidic outlet channels and the one or more microfluidic inlet channels at a rate selected from the group consisting of: between about 0.25 Hz and about 0.5 Hz, between about 0.5 Hz and about 0.75 Hz, between about 0.75 Hz and about 1 Hz, between about 1 Hz and about 2 Hz, between about 2 Hz and about 3 Hz, between about 3 Hz and about 4 Hz, between about 4 Hz and about 5 Hz, between about 5 Hz and about 6 Hz, between about 6 Hz and about 7 Hz, between about 7 Hz and about 8 Hz, between about 8 Hz and about 9 Hz, between about 9 Hz and about 10 Hz, and between about 10 Hz and about 20 Hz.

Another aspect of the invention includes a microfluidic pipette including: a substrate defining a microfluidic outlet channel, one or more microfluidic inlet channels, and a flow switching chamber configured to route one of more of a first fluidic input, a second fluidic input, and a third fluidic input to the microfluidic outlet channel; and a dispensing region located on the exterior of the substrate. Each of the microfluidic outlet channel and the one or more microfluidic inlet channels include an opening on the dispensing region.

This aspect of the invention can have a variety of embodiments. In one embodiment, the flow switching chamber routes the fluidic inputs through selective flow of a first switching fluid and a second switching fluid.

Another aspect of the invention provides a microfluidic pipette including: a substrate defining one or more microfluidic outlet channels and one or more microfluidic inlet channels; and a dispensing region located on the exterior of substrate. Each of the one or more microfluidic outlet channels and the one or more microfluidic inlet channels include an opening on the dispensing region such that a substance dispensed from the one or more outlet channels gathers and recirculates in the dispensing regions before being withdrawn by the one or more microfluidic inlet channels. A ratio of the distance between openings of the one or more microfluidic outlet channels and the edge of the substrate and a cross-sectional dimension of the one or more microfluidic outlet channels is between about 1:1 and about 5:1.

Still another aspect of the invention provides a microfluidic pipette including: a substrate defining one or more microfluidic outlet channels and one or more microfluidic inlet channels; and a dispensing region located on the exterior of substrate. Each of the one or more microfluidic outlet channels and the one or more microfluidic inlet channels include an opening on the dispensing region such that a substance dispensed from the one or more outlet channels gathers and recirculates in the dispensing regions before being withdrawn by the one or more microfluidic inlet channels. The distance between openings of the one or more microfluidic outlet channels and the edge of the substrate is less than a cross-sectional dimension of the one or more microfluidic outlet channels.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "microfabrication" is meant to refer to a set of techniques used for fabrication of micro- or nano-structures. In certain preferred embodiments, microfabrication includes, but is not limited only to, the following techniques: photolithography, electron beam lithography, laser ablation, direct optical writing, thin film deposition (spin-coating, spray coating, chemical vapor deposition, physical vapor deposition, sputtering), thin film removal (development, dry etching, wet etching), replica molding (soft lithography), or bonding.

By "microchannel" or "channel" is meant to refer to a tube with nano- or micro-scopic cross-section. In certain preferred embodiments, a microchannel or channel has a size in the range of 0.1-500 µm. In other preferred embodiments of the present invention, microchannels are fabricated into microfluidic devices by means of microfabrication.

By "microfluidic device" is meant to refer to the microfabricated device comprising microchannels or circuitries of microchannels, which are used to handle and move fluids. Preferably, microfluidic devices may include components like junctions, reservoirs, valves, pumps, mixers, filters, chromatographic columns, electrodes, waveguides, sensors etc. Microfluidic devices can be made of polymers such as polydimethylsiloxane (PDMS), poly(methyl methylacrylate) (PMMA), polytetrafluoroethylene (PTFE), polyethylene (PE) epoxy resins, and thermosetting polymers; amorphous materials (e.g., glass), crystalline materials (e.g., silicon, silicon dioxide); or metallic materials (e.g., aluminum, copper, gold, and silver, and alloys thereof). In certain preferred embodiments, a microfluidic device may contain composite materials or may be a composite material. The microfluidic pipette is a microfluidic device.

By "object of interest" is meant to refer to the material entity to be stimulated, studied, investigated or otherwise influenced by means of the microfluidic device. Exemplary objects of interest include cells.

By "sensor" is meant to refer to a device that detects the response of an object of interest. In one embodiment, the sensor detects a response to a stimulus controlled fully or partially by the microfluidic device, preferably a direct physically measurable response to a chemical stimulus, controlled fully or partially by the microfluidic device.

By "open volume" is meant to refer to the liquid reservoir that holds the objects of interest.

By "open volume container" is meant to refer to physical boundaries of the liquid open volume. Preferably, these boundaries comprise three-dimensional boundaries such as full or partial enclosures, two-dimensional boundaries such as surfaces, capillary outlets defining suspended droplets.

By "channel exit" is meant to refer to an open end of a channel that leads into the open volume.

By "channel entrance" is meant to refer to an open end of a channel that does not lead into the open volume. Channel entrances typically lead into reagent reservoirs or connections to the control interface.

By "channel outlet" is meant to refer to a channel exit through which outflow flows from the pipette into the open volume.

By "channel inlet" is meant to refer to a channel exit through which inflow flows from the open volume into the pipette.

By "flow recirculating microfluidics device" is meant to refer to a microfluidic device where the outflow of one or more channel outlets is circulating fully or partially back into the microfluidics device through one or more channel inlets.

By "recirculation zone" is meant to refer to the fraction of the open volume that is exchanged by outflow from the flow recirculating microfluidics device.

By "free-standing microfluidic device" is meant to refer to a microfluidic device that does not have a fixed connection to the open volume, but can be moved and positioned independently from and relative to the open volume.

By "positioning device" is meant to refer to a device, which moves an object attached to it in three-dimensional space. In one embodiment, the positioning device moves the object along three axes, e.g., in the x, y, and z directions. In another embodiment, the positioning device rotates the object.

By "pipette" is meant to refer to a liquid volume dispensing device.

By "tapered pipette" is meant to refer to a liquid volume dispensing device, featuring the outlet at a tapered end. A "tapered end" is meant to refer to one end of the pipette that is smaller in diameter than the other end. In certain embodiments, a tapered end is in the size range of 1-1000 μm.

By "channel exit plane" is meant to refer to a plane, which interfaces the channel with the open volume.

By "multiple fluid components" is meant to refer to the components of a recirculation zone. In certain preferred embodiments, multiple fluid components are defined as either multiple different concentrations of a single chemical constituent or multiple chemical constituents of the same or different individual concentrations.

DESCRIPTION OF THE DRAWINGS

FIGS. 1A and 1B are schematic views of the pipette, held by a micromanipulator and operating in an open volume on a microscope table. Components are numbered according to an exemplary fabrication sequence.

FIGS. 3A-3E shows simultaneous flow recirculation. FIG. 3A shows schematics of directed recirculated flows. FIG. 3B shows the concentration profile of the recirculation zone, showing fluorescein concentration vs. position from the channel outlet. FIGS. 3C-3E show fluorescence micrographs (fluorescein) of the microfluidic pipette in recirculation operation showing 50 μm channels at different recirculation pressures. FIG. 3C depicts recirculation at 102 mBar/−279 mBar. FIG. 3D depicts recirculation at 235 mbar/−279 mBar. FIG. 3E depicts recirculation at 81 mBar/−74 mBar.

FIG. 8, Panel A shows front (top panel) and side (bottom panel) views of a device featuring in-plane channel exits with respect to the device bottom plane. FIG. 8, Panel B shows front (top panel) and side (bottom panel) views of a device featuring through-plane channel exits with respect to the device bottom plane. (Exits are perpendicular to the device bottom plane).

FIG. 16A shows solution exchange around a single cell immobilized on an unstructured planar surface. The cell is exposed to pulsed or continuous chemical stimuli only inside the recirculation zone. Cells outside the recirculation zone are not suitably affected. One important adjustable parameter of chemical stimuli is stimulant concentration. FIG. 16B shows solution exchange around a single cell immobilized on a patterned or structured surface. FIG. 16C shows solution exchange around a single cell immobilized on a planar surface and contacted by surface-embedded electrodes. FIG. 16D shows solution exchange around a single cell immobilized on a planar surface and connected to a planar patch-clamp device. FIG. 16E shows simultaneous solution exchange around several cells co-immobilized on a planar surface in appropriate distance. FIG. 16F shows stimulation of localized parts of a cell-network, such as a neuronal cell network. Other parts of the network are simultaneously monitored for their response. FIG. 16G shows application of a concentration gradient of a chemical in order to stimulate a cell and cause chemotaxis along the gradient. FIG. 16H shows electroporation of a surface-immobilized single cell using an electrical filed generated by means of electrode pairs embedded in the pipette. FIG. 16I shows phospholipid mono- or bilayer migration (spreading) towards the recirculation zone, following an artificial chemotaxis scheme. FIG. 16J shows application of multiple fluid components in multiple independent recirculation zones, targeting different individual nodes of a vesicle nanotube network.

FIG. 24A provides a schematic representation of a microscopy imaging setup, where the microfluidic device is positioned on top of a biological tissue culture, which is being penetrated by the recirculation zone. FIG. 24B provides a fluorescence wide-field micrograph of an organotypic tissue slice (rat cerebral cortex) penetrated by the recirculation zone containing fluorescein. FIG. 24C depicts fluorescence intensity vs. time relationship for pulsed exposure of the tissue slice depicted in FIG. 24B, demonstrating the generation of concentration waves by the microfluidic device.

FIGS. 25A-25D depict a schematic of structure and operation of a microfluidic pipette according to one embodiment of the invention.

DETAILED DESCRIPTION

Embodiments of the invention provide devices and methods for suitably controlling solution environments at the micro-scale. The invention relates, generally, to microfluidics and provides methods for the fields of physics, chemistry, biology, and medicine, where chemical manipulations with microscale objects, just like cells or artificial sensors, is desirable.

The present invention features, in one aspect, a microfluidic pipette, where a flow circulation regime is used to suitably eliminate cross-contamination and contamination of the open volume, and enable high-resolution spatial control of concentration very close to selected microscopic objects, preferably singly-selected microscopic objects, such as a single cell, a cell network (e.g., a neuronal network or an artificial microscopic sensor), or groups of objects (e.g., a complete nanotube-vesicle network).

The present invention features a point of exposure that is free-standing and not coupled to a given reservoir, and, accordingly, the point of exposure can preferably be set by external mechanical positioning devices such as micromanipulators or on-chip actuators, which move the microflow pipette into position at the chosen point and allow it to be moved around during an experiment, if desirable. Preferably, as flow switching can be easily incorporated in a given microfluidics design, the device comprises fast solution exchange capability. Since the microfluidics laminar flow-regime allows the generation of gradients, which are suitably well-controlled by molecular diffusion, the device has the capability to suitably generate and adjust gradients in a small, localized volume close to any arbitrary chosen object of interest.

Preferably, since the device is working in a circulation or recirculation regime, all the products liberated from the exposed object, for example, due to chemical or biological processes associated with product formation, are captured by the restricted flow and circulated back into the microfluidics device, which can have purification, concentration and detection capabilities (e.g., capillary electrophoresis, chromatography, immune affinity separation using magnetic beads, evaporative concentration, electrochemical detection, fluorescent detection, mass spectrometry, and the like).

In one aspect, the present invention features a free-standing pipette, comprising a microfluidic device comprising one or more channels with exits leading into an open-volume.

In certain preferred embodiments, the pipette is tapered at one end.

Figures 1A, 1B:
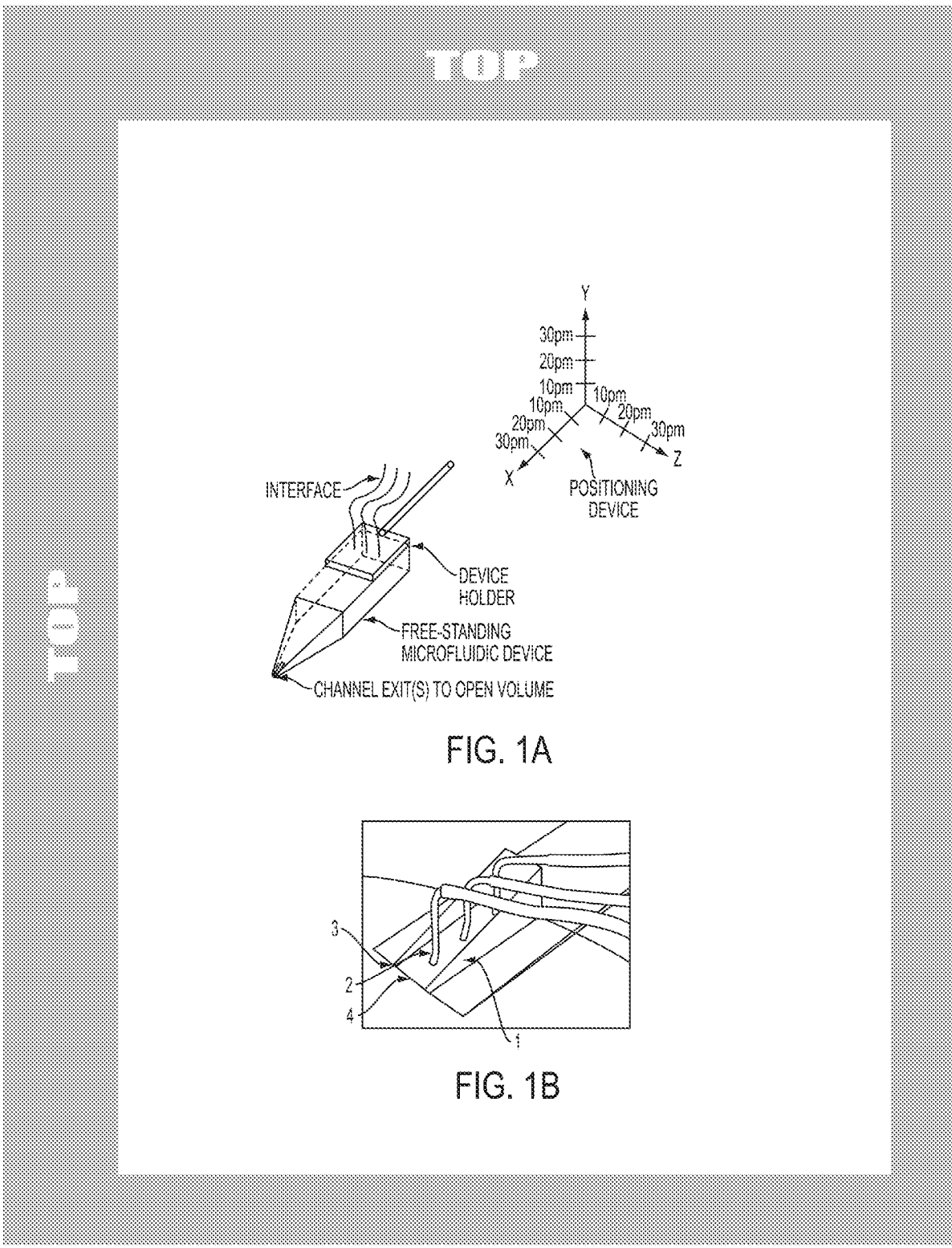
FIGS. 1A and 1B depict an exemplary general layout of the free-standing microfluidic pipette.

This device is exemplified according to preferred embodiments, for example, in FIGS. 1A and 1B.

Figures 2A, 2B, 2C, 2D, 2E:
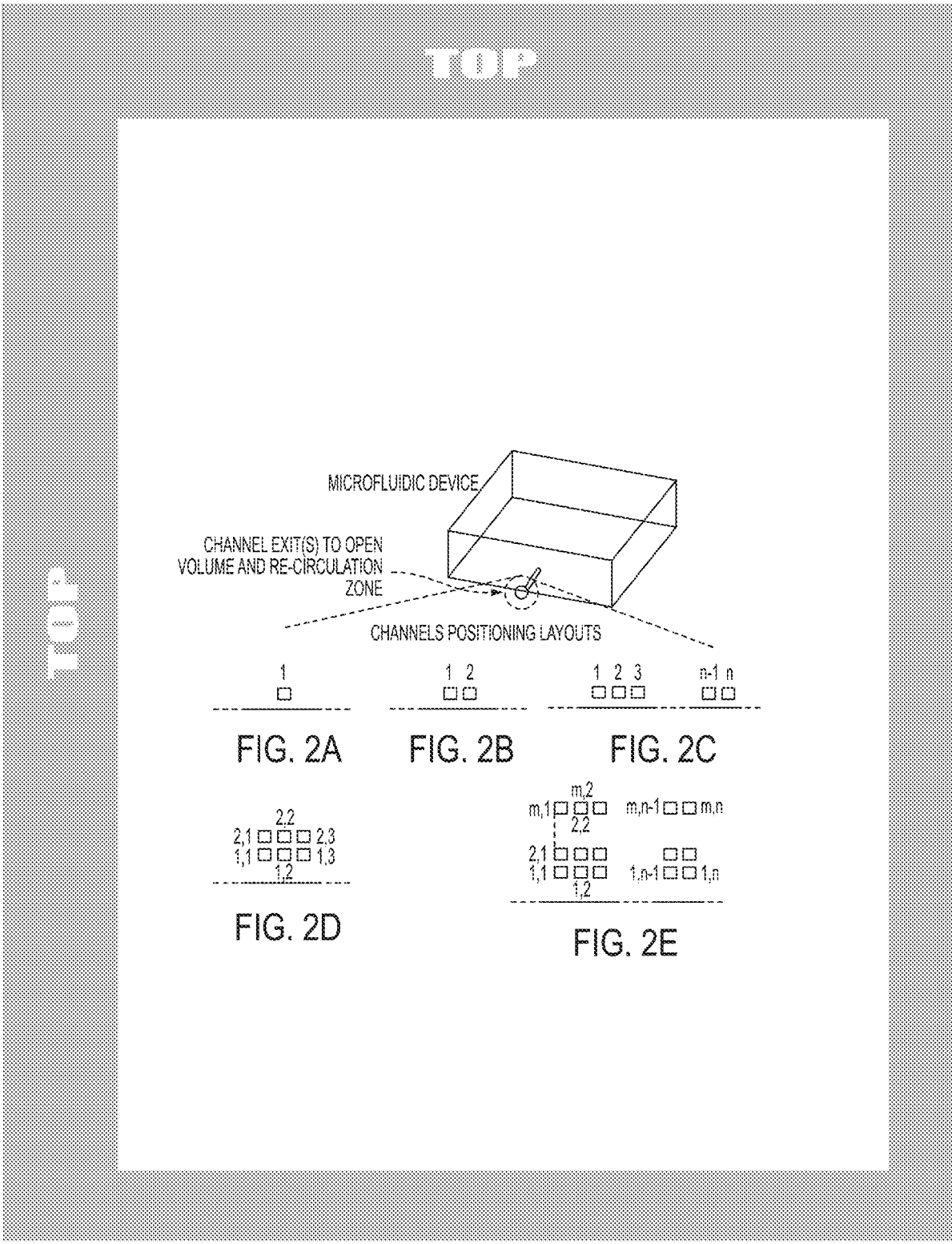
FIGS. 2A-E provide an exemplary illustration of channel configurations. Different arrangements in a linear (FIGS. 2A-2C) and matrix-like fashion (FIGS. 2D-2E) are shown.

Preferably, the microfluidic device has at least one channel outlet (FIG. 2A), but possibly multiple channel outlets aligned in a one-dimensional array (FIG. 2B-C) or in two-dimensional array (FIG. 2D-E) leading to the open volume.

Preferably, the flow circulation can be arranged in simultaneous or sequential manner, or as a combination of both.

In certain preferred embodiments, the simultaneous flow circulation, for example as shown in FIGS. 3A and 3C-3E comprises at least two channels that are preferably aligned next to each other, where one channel preferably functions as a flow outlet, while another channel preferably functions as a flow inlet. Preferably, through the flow outlet, fluid is flowing from the channel into the open volume (outflow). Preferably, through the flow inlet, fluid is flowing from the open volume into the chip (inflow).

According to certain exemplary embodiments, if sufficient inflow is suitably maintained relative to outflow, a static flow circulation zone is formed (FIG. 3A). Preferably, apart from very small diffusion losses, all the fluid leaving the device is recirculating into it. The volume of the recirculation zone remains constant (static recirculation zone). According to certain preferred embodiments of the present invention, the chemical composition inside the circulation zone corresponds to the composition of the outflow stream while the composition outside the circulation zone corresponds to composition of the open volume solution (FIG. 3B). Preferably, these two regions are separated by a diffusive layer. Diffusion losses result from loss of material from the recirculation zone by diffusion through the diffusion layer.

According to certain preferred embodiments of the present invention, the size of the circulation zone depends on the device layout, and on the inflow and outflow flow rates, respectively. Preferably, the size of the circulation zone can be adjusted during pipette operation by adjusting the inflow to outflow ratio (FIGS. 3C-3E). Further, the thickness of the diffusive layer depends on the diffusivity and flow rate in the circulation zone. Preferably, under stable operation conditions, the spatial distribution of substance concentration in the recirculation zone can be suitably maintained over time (concentration distribution is time independent). Without circulation, the concentration distribution cannot be suitably maintained due to the diffusion that counteract with concentration gradients.

Figure 4:
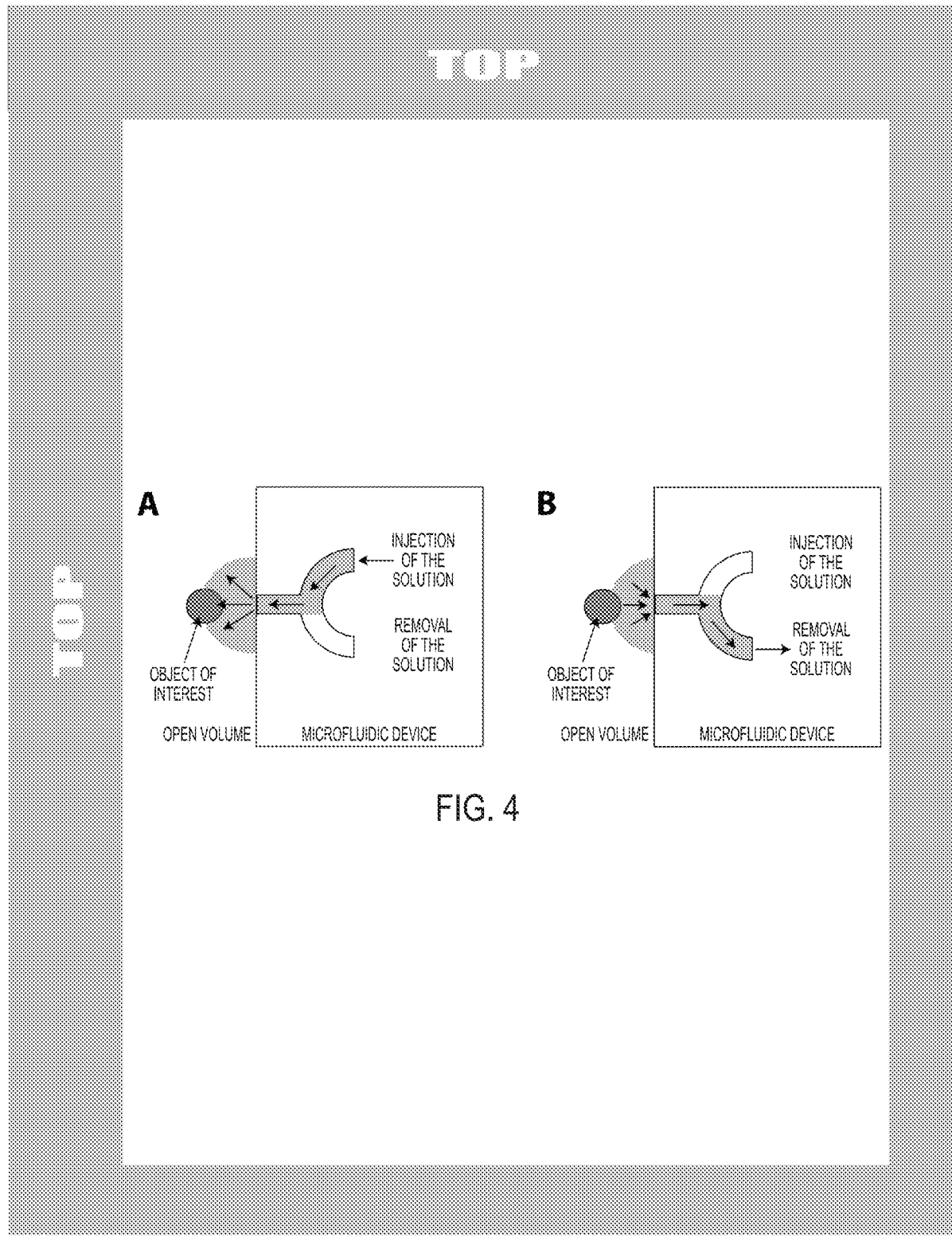
FIG. 4 is an exemplary illustration of sequential recirculation. Panel A shows that during the first step of the cycle, solution is injected around the object. Panel B shows that during the second step of the cycle, solution is circulated back to the device.

According to further preferred embodiments, the sequential flow circulation, which is depicted in FIG. 4, needs at least one channel outlet with an operation cycle containing at least two steps. In a preferred embodiment, during the first step, solution is suitably injected to the open volume, creating a dynamic recirculation zone. It replaces temporarily the open volume solution inside a microscopic region around the channel outlet (FIG. 4, Panel A). In a further related embodiment, the second step involves withdrawal of the recirculation zone into the same device (FIG. 4, Panel B).

FIG. 4 shows a device where the sequential flow circulation is achieved by switching a single channel sequentially from outlet to inlet. Static spatial distribution cannot be maintained with the sequential flow circulation. The sequence of injection and retracting the recirculation zone can be continuously repeated (operation cycle), creating a pulsating recirculation zone. It can be used for the exposure of a microscopic target object with a substance, avoiding loss of the substance into the open volume. According to preferred embodiments of the present invention, simultaneous and sequential circulations can be suitably combined, in a device comprising at least 2 channel outlets into the open volume. In certain preferred embodiments, the volume of the recirculation zone can be made time dependent by varying the rates of inflow and outflow.

Figure 5:
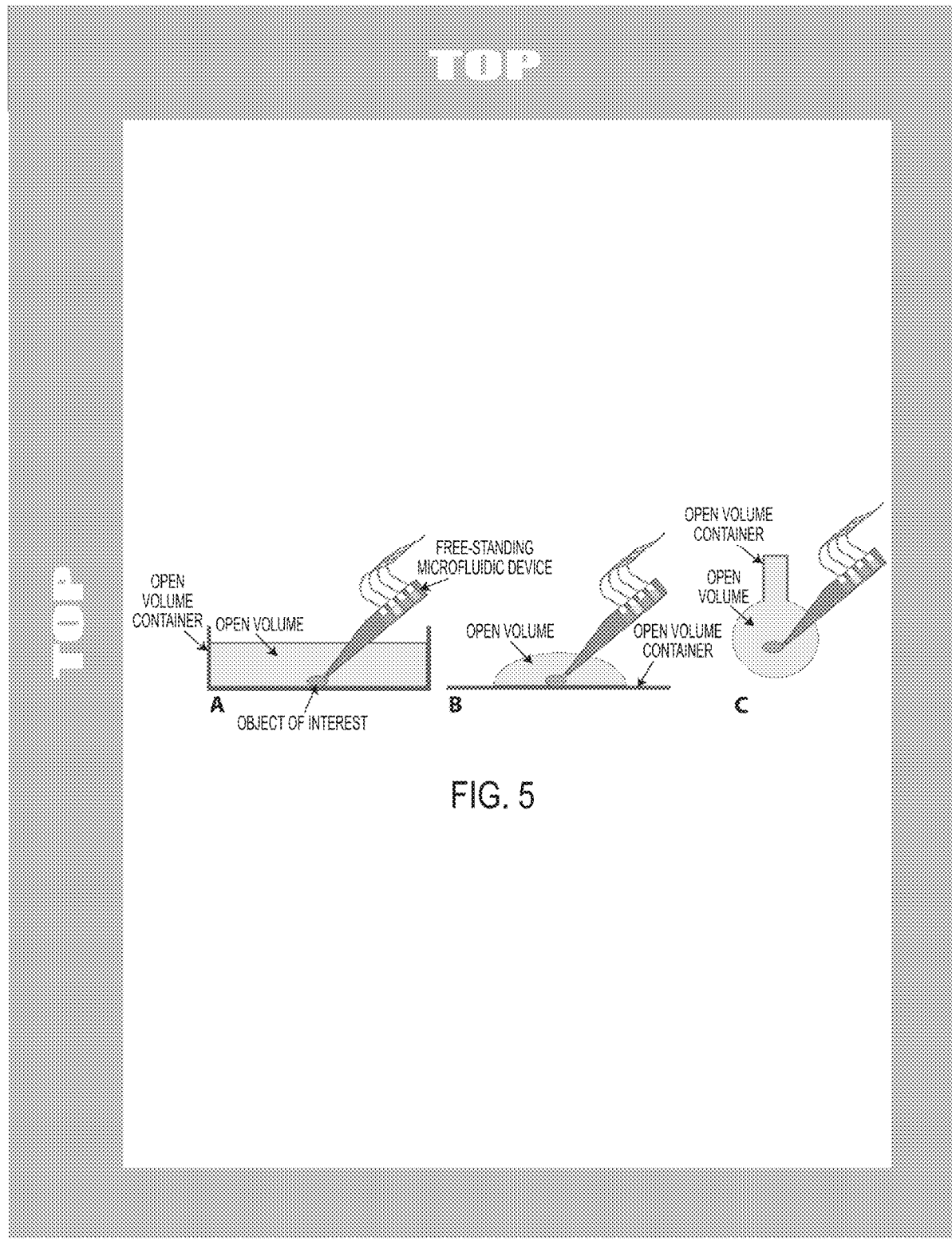
FIG. 5 is an exemplary illustration of possible open volume containers.

According to certain exemplary embodiments, the pipette can be applied in a variety of different open volume environments. FIG. 5 depicts three non-limiting examples of open volume reservoirs and containers. In certain preferred embodiments, open volumes comprise sample containers, such as cell-culture dishes (FIG. 5A), supported open volumes such as open droplets (FIG. 5B) and suspended volumes such as free-hanging droplets at capillary orifices (FIG. 5C). Preferably, the open volumes are independent from the pipette, and can be freely exchanged during pipette operation. According to further preferred embodiments, several pipettes can simultaneously and independently operate in the same open volume.

Figure 6:
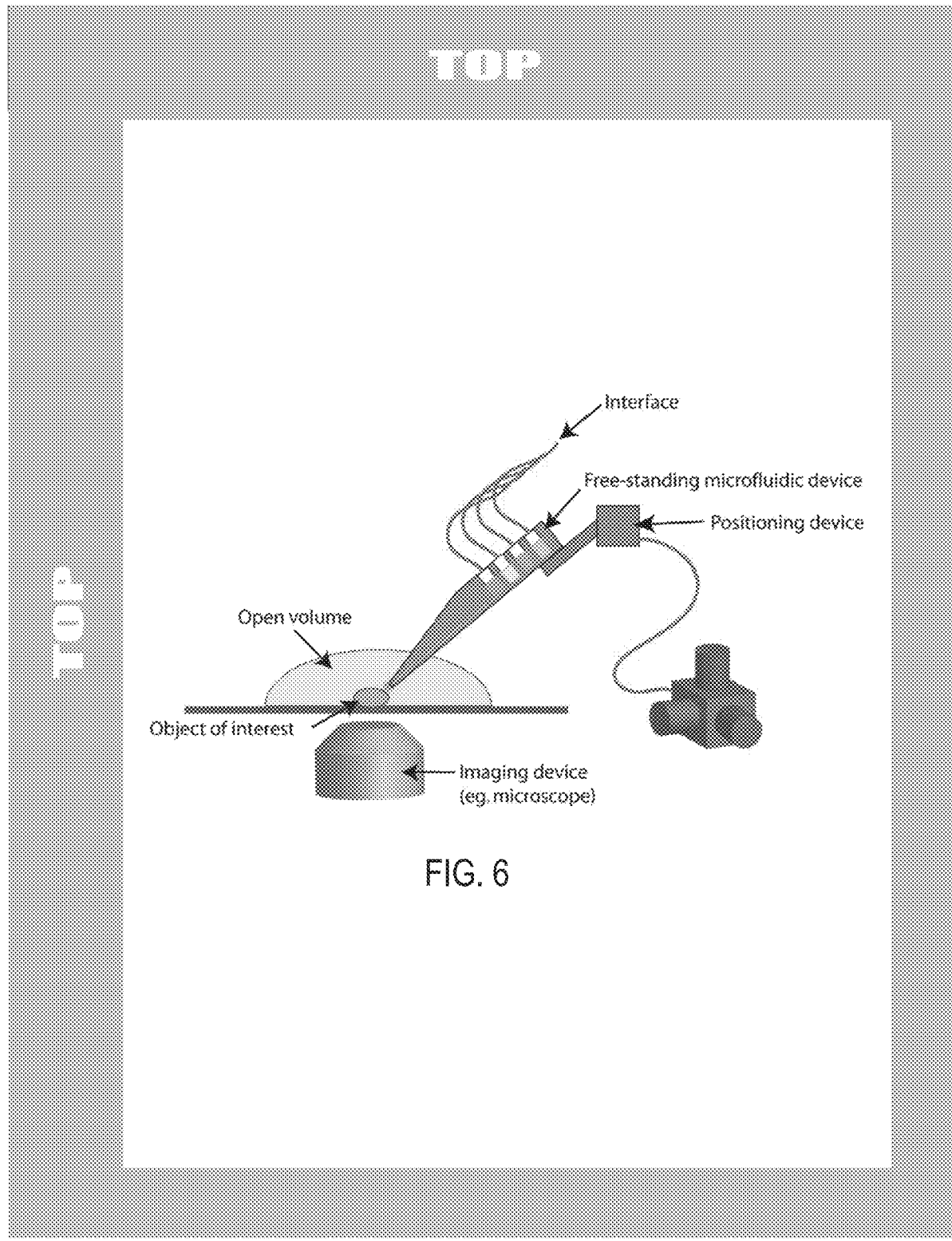
FIG. 6 provides exemplary illustrations of components of an example experimental setup for operating the microfluidic pipette under an inverted microscope. The object of interest is, in this case, suspended in an open droplet on a microscope coverslip.

According to certain preferred embodiments of the invention, a preferred example of a minimal setup required to operate the pipette is depicted in FIG. 6. In certain exemplary embodiments, the pipette is applied in a microscopy environment, immersed in an open droplet on a microscopic coverslip. Preferably, the positioning of the pipette is achieved by micromanipulation tools, such as mechanical, piezoelectric or hydraulic micromanipulators. These can be controlled in x, y and z dimension and used to precisely (within 10s of nm) position the pipette outlet at a desired location. The pipette is interfaced to its flow control circuitry. Non-limiting examples of such control interface are electrical, fluidic or pneumatic control lines. The target objects are suspended in the open droplet and can be visualized through the microscope optics. The same optics are applied in this non-limiting example to monitor the recirculation zone.

Figure 7:
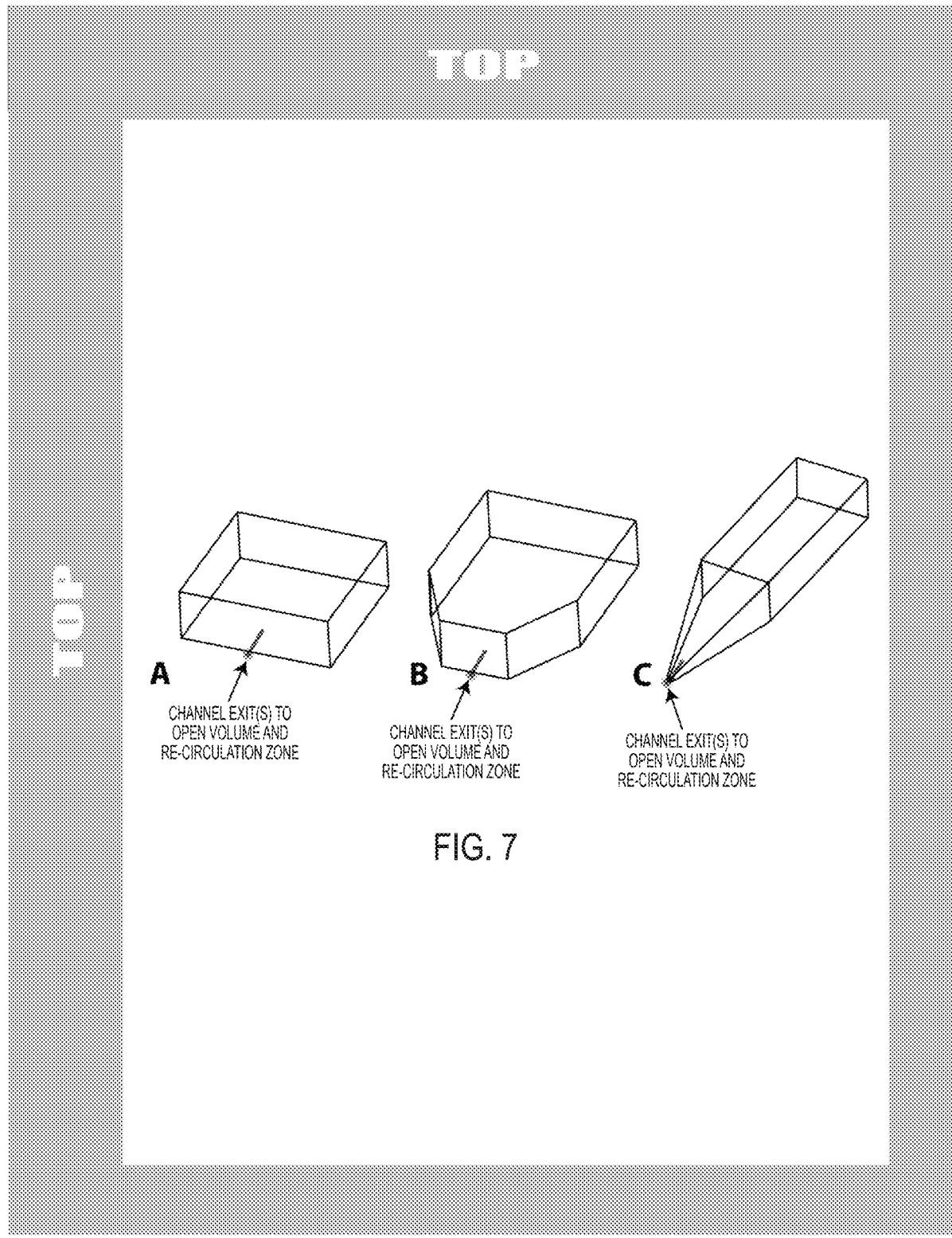
FIG. 7 provides exemplary illustrations of pipette shapes, where the shape depends on the mode of operation according to a specific application. Panel A illustrates an exemplary broad block type device. Panel B illustrates an exemplary partly pointed device. Panel C illustrates an exemplary strongly pointed device, suitable for very small volumes, such as open droplets.

According to preferred exemplary embodiments, the geometry of the microfluidic pipette in the region around the channel outlets and inlets can be suitably adjusted to the application requirements. FIG. 7 shows preferred examples of channel exit region geometries according to exemplary embodiments of the invention. Preferably, the simplest geometry is a block-like geometry that can be most conveniently fabricated (FIG. 7, Panel A). For applications with a low number of objects of interest in a given volume, such geometry can be applied without interfering or damaging objects of interest. Preferably, if the number of objects of interests is large, the pipette channel outlet area can be shaped into smaller geometries to minimize space requirements. FIG. 7B shows a pipette with a trapezoid tip of dimensions much larger than the channel exit area. Preferably, such a geometry has a smaller footprint compared to the block-like geometry, and can be applied in open volumes with intermediate object density or in open volume containers of limited size. FIG. 7C shows a pipette of elongated trapezoid geometry, where the channel exit area is not considerably smaller than the pipette tip. Preferably, such geometry can be applied under conditions where the density of objects of interest in the open volume is very large, as in the case of cell cultures in culture dishes, or when the open volume container size is severely limited, for example, in suspended droplets.

Figure 8:
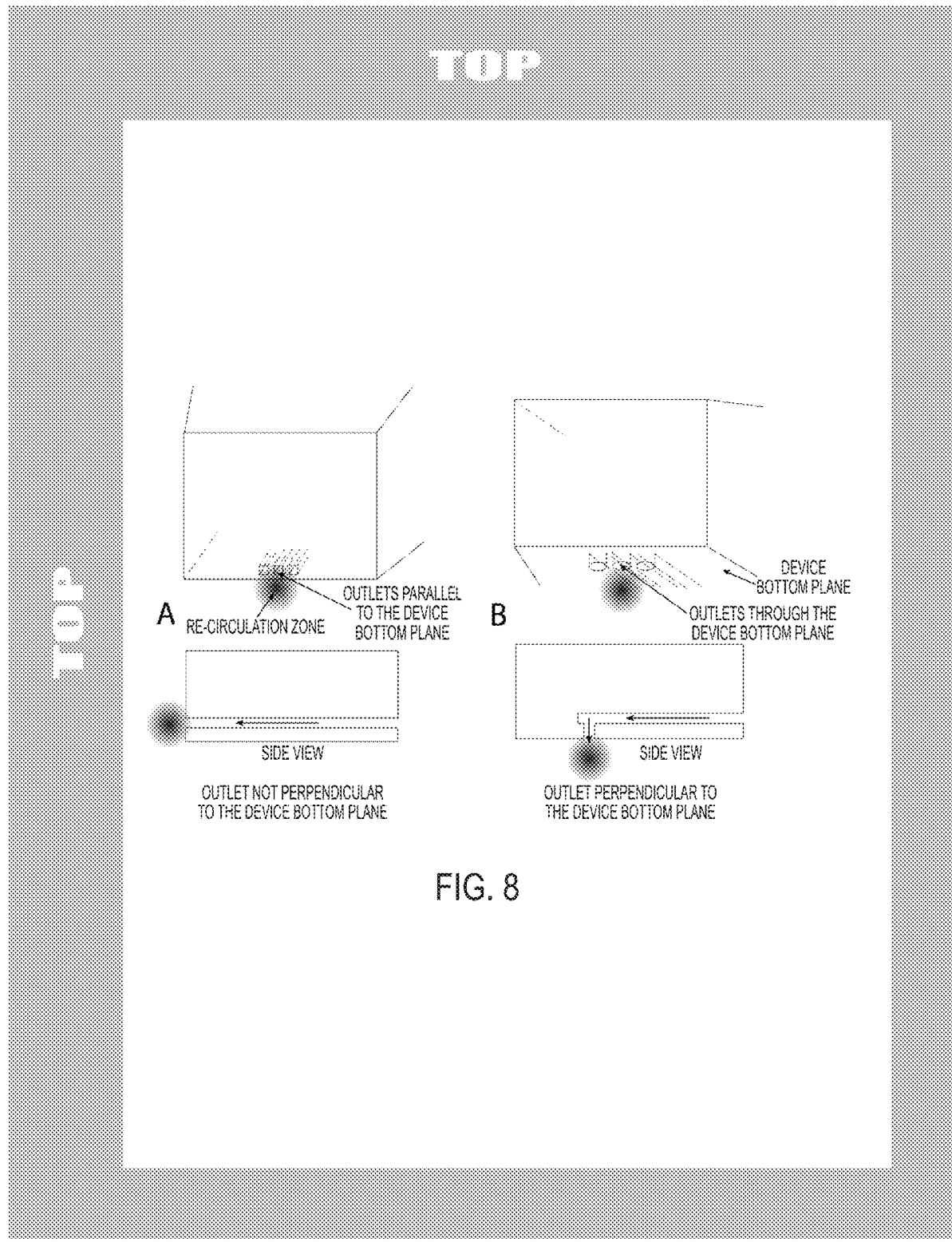
FIG. 8 depicts exemplary illustrations of channel arrangements with respect to the device geometry.
Figure 9:
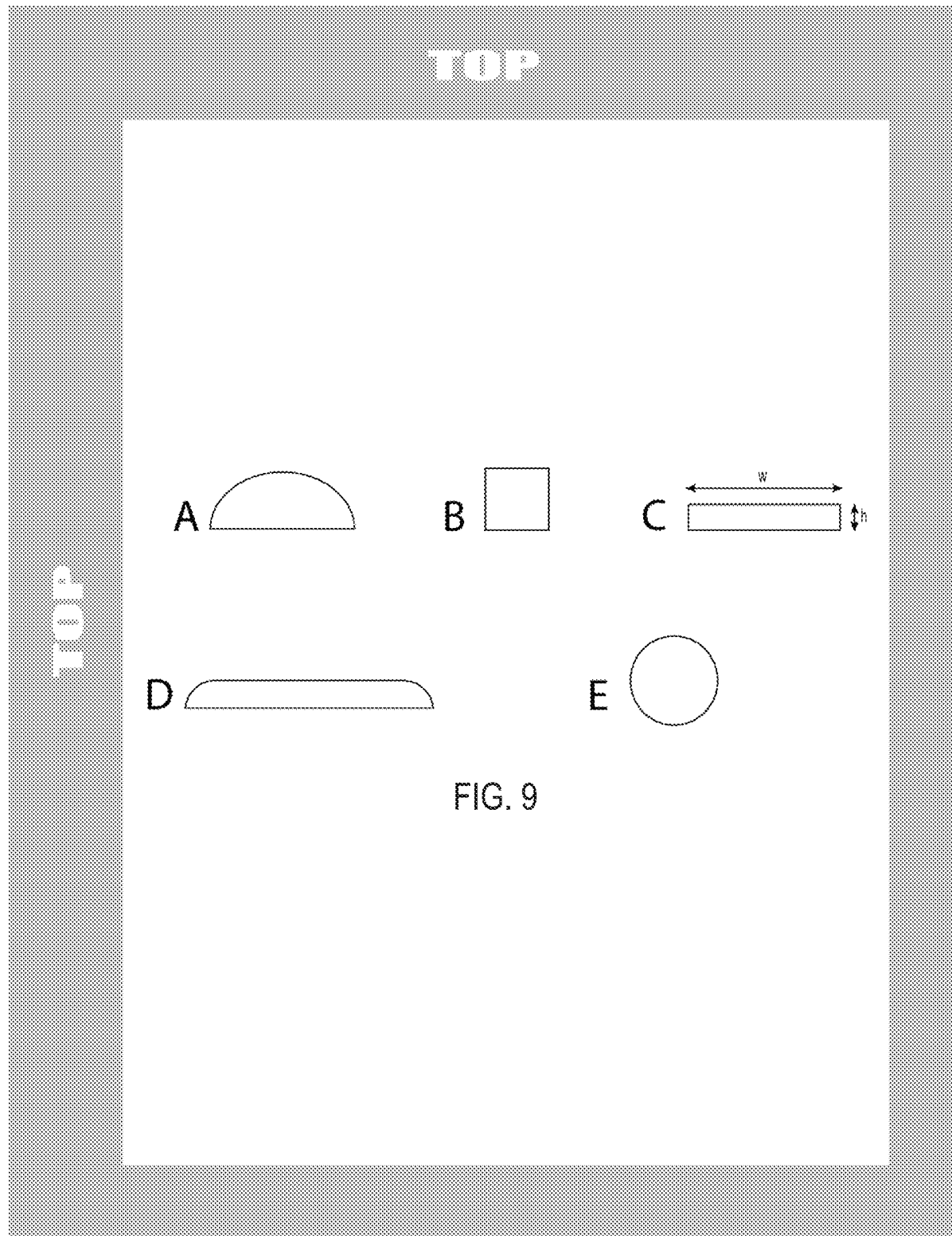
FIG. 9 provides exemplary illustrations of cross-section shapes of channel outlets. Exemplary channel cross-sections include partly-rounded (FIG. 9, Panels A and D), polygonal (FIG. 9, Panels B and C), and circular (Panel E).

According to further exemplary embodiments, the channel in- and outlets may be suitably positioned along the main axis of the device, i.e., in-plane with the main axis of the device. For example, such a channel configuration is depicted in FIG. 8, Panel A. Alternatively, in other exemplary embodiments, channel inlets and outlets can be positioned in an angle from the main axis of the chip, for example, through the bottom plane in a 90° angle (FIG. 8, Panel B). These different arrangements of channel exits facilitate the positioning of the pipette towards the object of interest in certain applications. Preferably, the shapes of channels in the microfluidics pipette can be arbitrarily chosen. Some limitations might be imposed by fabrication procedures, such as photoresist geometries with a square or rectangular cross-section on the fabrication master. FIG. 9 shows non-limiting examples of possible channel geometries. Channels with partly rounded (FIG. 9, Panels A and D), polygonal (FIG. 9, Panels B and 9C) or circular cross-sections (FIG. 9, Panel E) can be fabricated.

Figure 10:
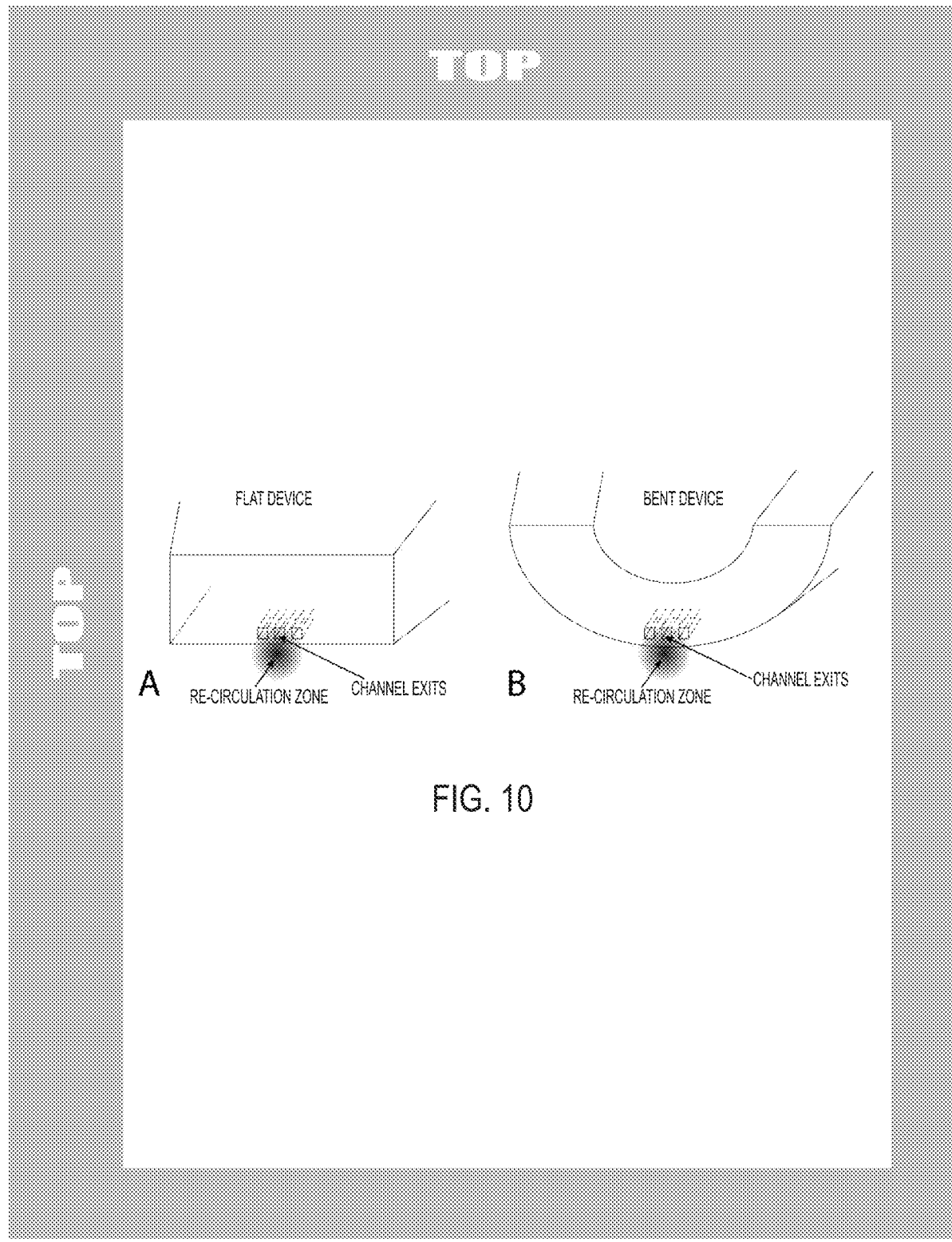
FIG. 10 shows a planar (flat) device geometry (Panel A) and a non-planar (bent/curved) geometry (Panel B).

According to further preferred embodiments, the three-dimensional shape of the pipette device is initially defined by the fabrication procedure. Preferably, this results typically in a planar overall device geometry (FIG. 10). The stability of a pipette is suitably improved by a non-planar geometry. Thin, planar devices can be fabricated from soft materials (FIG. 10, Panel A) and forced into a non-planar geometry (FIG. 10, Panel B), improving stability significantly. Alternatively, in other certain embodiments, the pipette can be fabricated in a non-planar geometry from the beginning. This is also applicable to other than soft materials. A non-limiting example of the non-planer geometry is a curved geometry (FIG. 10, Panel B).

Figure 11:
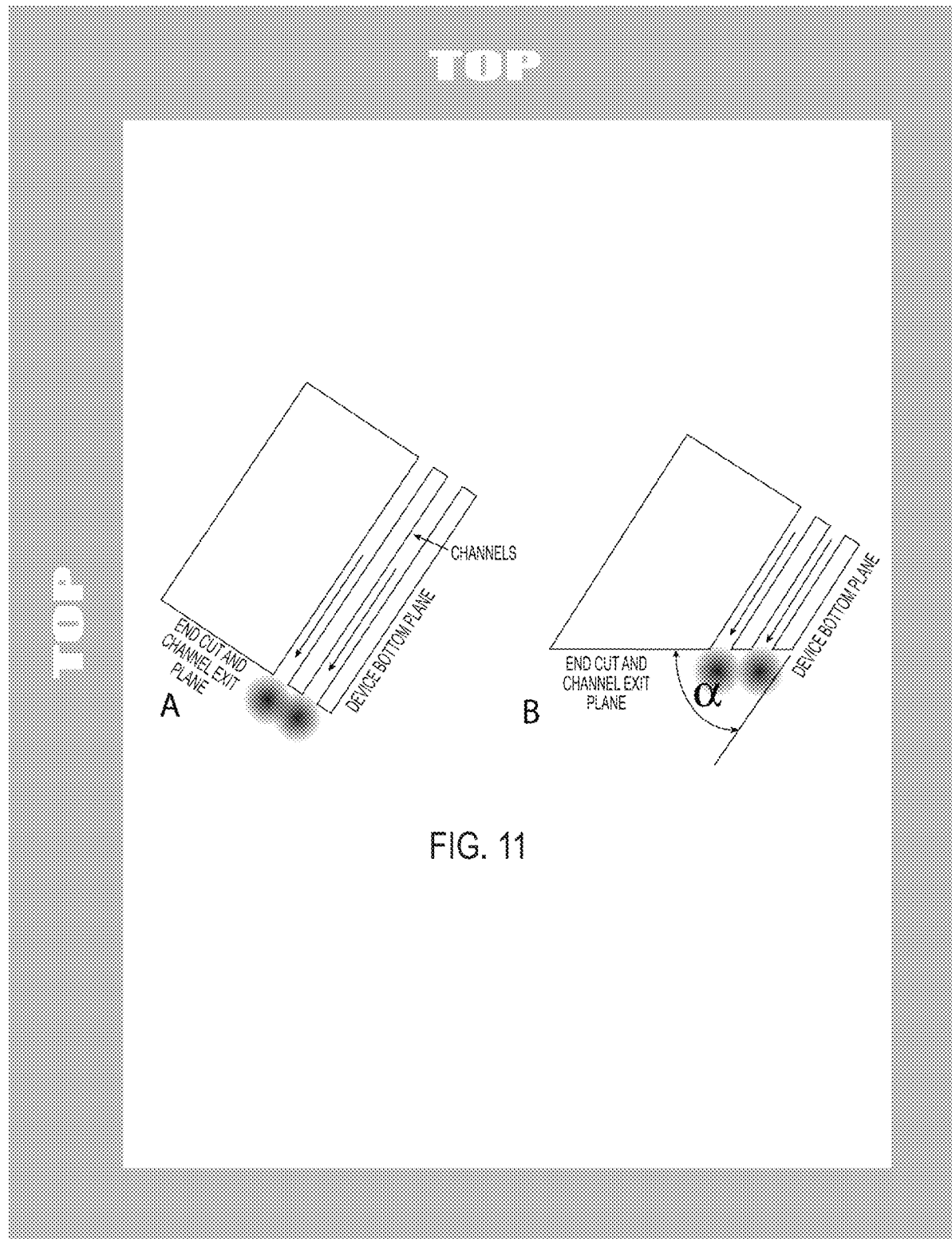
FIG. 11 depicts exemplary channel exit planes according to preferred embodiments of the present invention.

In certain preferred embodiments, the pipette is optionally provided with an end-cut to define the orientation of the channels towards the objects of interest in the open volume. For example, in the simplest case, the end-cut is 90° with respect to the bottom plane of the device (FIG. 11A). Alternatively, an end-cut with an angle α with respect to the bottom plane is applied (FIG. 11B). The angular end-cut is chosen with respect to the preferred orientation of the main axis of the chip towards the objects of interest, bringing the channel exits closer to the objects of interest compared to a 90° end-cut. For example, if the pipette main axis is oriented in a 45° angle against the surface holding objects of interest, a 45° end-cut will orient the channel exits parallel to this surface, allowing close proximity.

Figure 12:
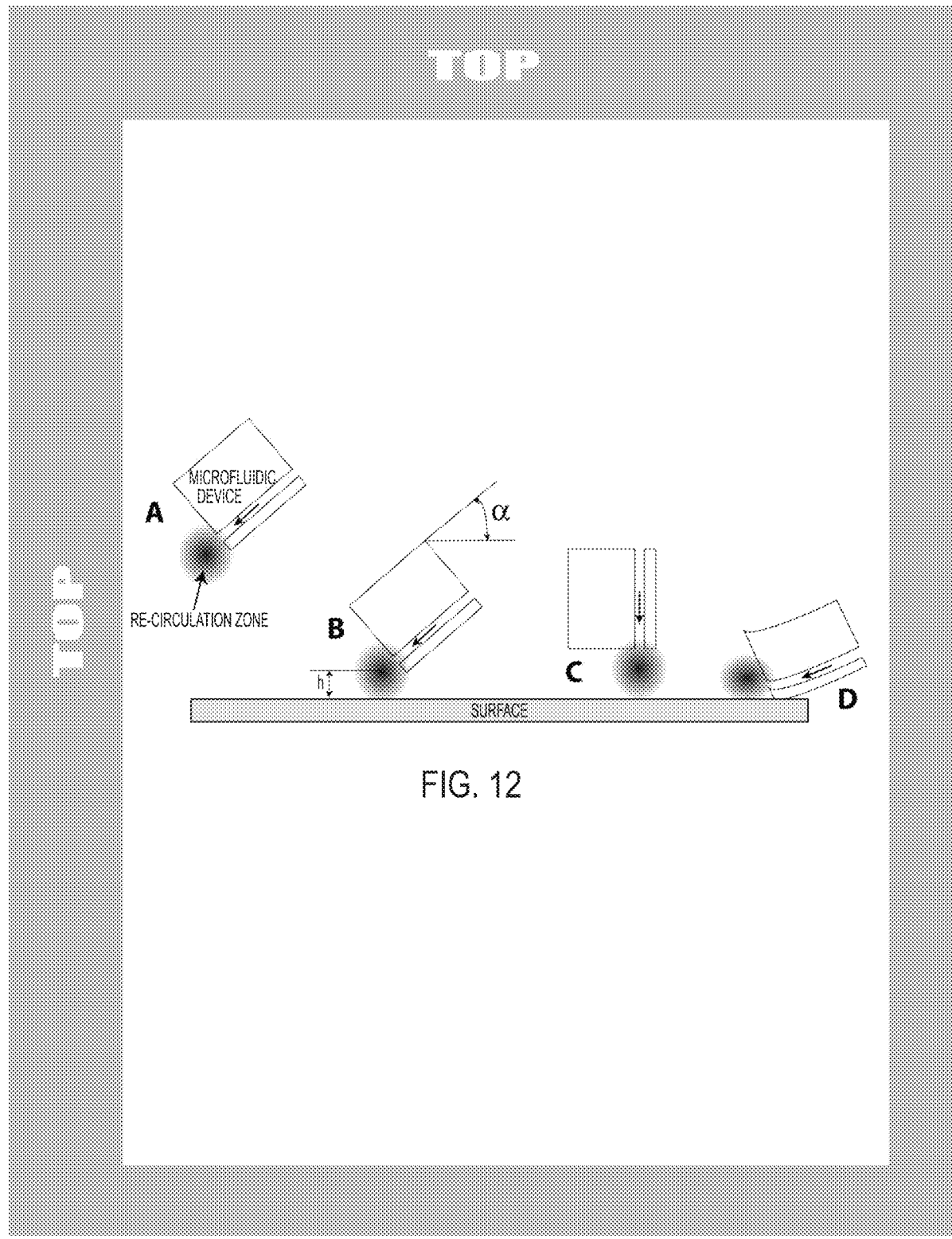
FIG. 12 depicts exemplary illustrations of the positioning of the microfluidic pipette with respect to the boundaries of an open volume.

Preferred examples of the positioning of the microfluidic pipette with respect to the boundaries of an open volume are depicted in FIG. 12, although the invention is not limited only to the illustrated examples. Preferably, the pipette can be away from the boundary or in close proximity to it. FIG. 12A shows an example of positioning the pipette in the open volume, away from a surface. The recirculation zone does not reach a solid boundary. FIG. 12, Panels B and C show examples of positioning the pipette at a distance h from the surface of an open volume. Preferably, the recirculation zone reaches the surface, but the device is not in direct mechanical contact. In FIG. 12, Panel D the device is in direct mechanical contact with the surface, providing additional mechanical stability. The recirculation zone also reaches the surface.

Figure 13:
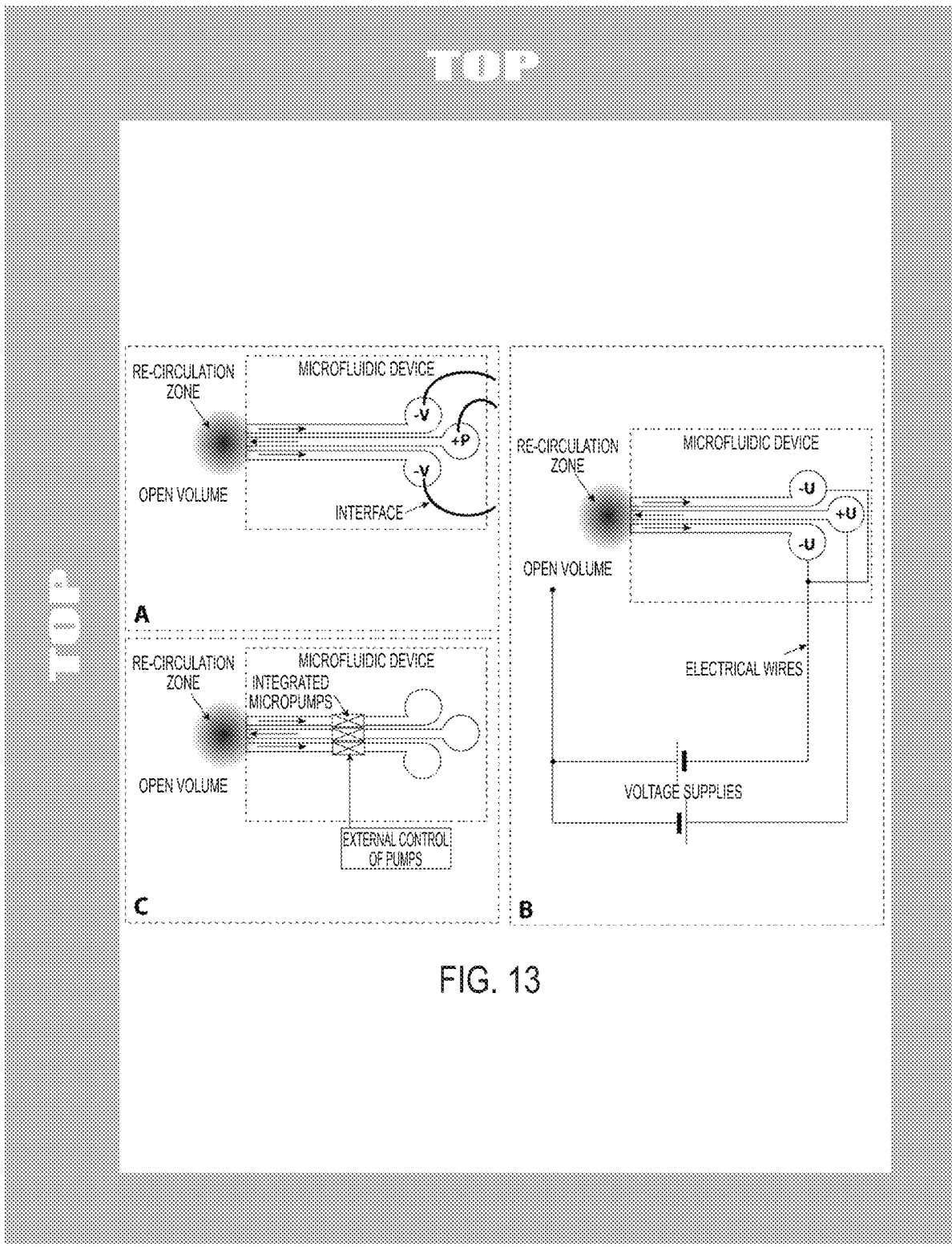
FIG. 13 depicts exemplary illustrations of flow driving mechanisms. Panel A shows external driving by pressure. Panel B shows external driving by an applied electric field. Panel C shows internal driving by on-chip pumps.

According to certain preferred embodiments of the invention, fluid flow in the device can, in a non-limiting way, be driven by different mechanisms, which are illustrated in FIG. 13. In one embodiment, fluids can be driven with external hydrostatic or pneumatic pressures (FIG. 13, Panel A). Reduced pressure, as compared to atmospheric pressure, withdraws solution from the open volume, while higher pressure injects a flow into the open volume. Preferably, flow rates in these devices are depending on channel geometry, fluid viscosity and applied pressures. Pressures can be created and controlled by various standard components, such as, but not limited to, pumps, valves, pressurized gas cylinders, and hydrostatic columns. In another embodiment, an electric-field can be applied to the microchannels, causing an electro-osmotic flow in these channels, which can be used to drive liquids (FIG. 13, Panel B). In another embodiment, pumps can be integrated into the microfluidic device itself. Preferably, micro-peristaltic pumps in PDMS devices are suitable non-limiting examples for such integrated devices (FIG. 13, Panel C).

Figure 14:
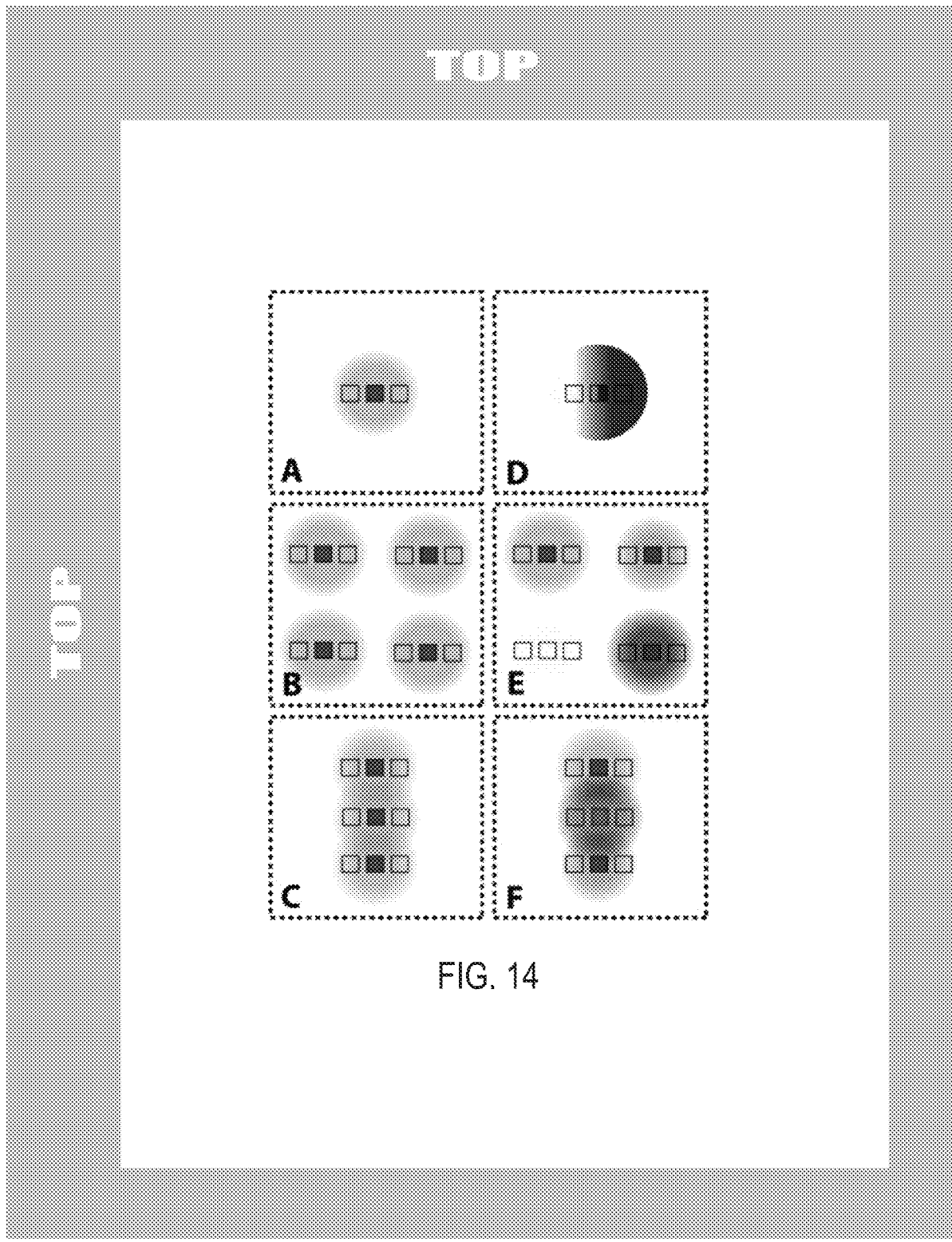
FIG. 14 illustrates dimensionality of pipette application: single and multiple fluid components, single and multiple recirculation zones. Panel A shows a single fluid component in a single recirculation zone. Panel B shows single fluid component in multiple individual recirculation zones. Panel C shows single fluid component in merged recirculation zones. Panel D shows multiple fluid components in a single recirculation zone. Panel E shows multiple fluid components in multiple individual recirculation zones. Panel F shows multiple fluid components in merged recirculation zones (gradient formation). Multiple components are defined as either multiple different concentrations of a single chemical constituent or multiple chemical constituents of the same or different individual concentrations.

According to further preferred embodiments, the pipette can operate in several different general modes of operation, depending on the number of fluid components, number of recirculation zones and the interconnection between individual recirculation zones. FIG. 14 depicts certain exemplary modes of operation, although it is to be understood that the invention is not limited by such. In particular, FIG. 14 depicts a single fluid component, single recirculation zone (FIG. 14, Panel A), single fluid component, multiple individual recirculation zones (FIG. 14, Panel B), single fluid component, merged recirculation zones (FIG. 14, Panel C), multiple fluid components, single recirculation zone (FIG. 14, Panel D), multiple fluid components, multiple individual recirculation zones (FIG. 14, Panel E), and multiple fluid components, merged recirculation zones, multicomponent gradients (FIG. 14, Panel F). Preferably, fluid components in this context are material constituents of fluid flows. Preferably, examples include, but are not limited to, liquids, pure solutions, mixed solutions, colloidal solutions, and suspensions. Multiple components are defined as either multiple different concentrations of a single chemical constituent or multiple chemical constituents of the same or different individual concentrations.

Figure 15:
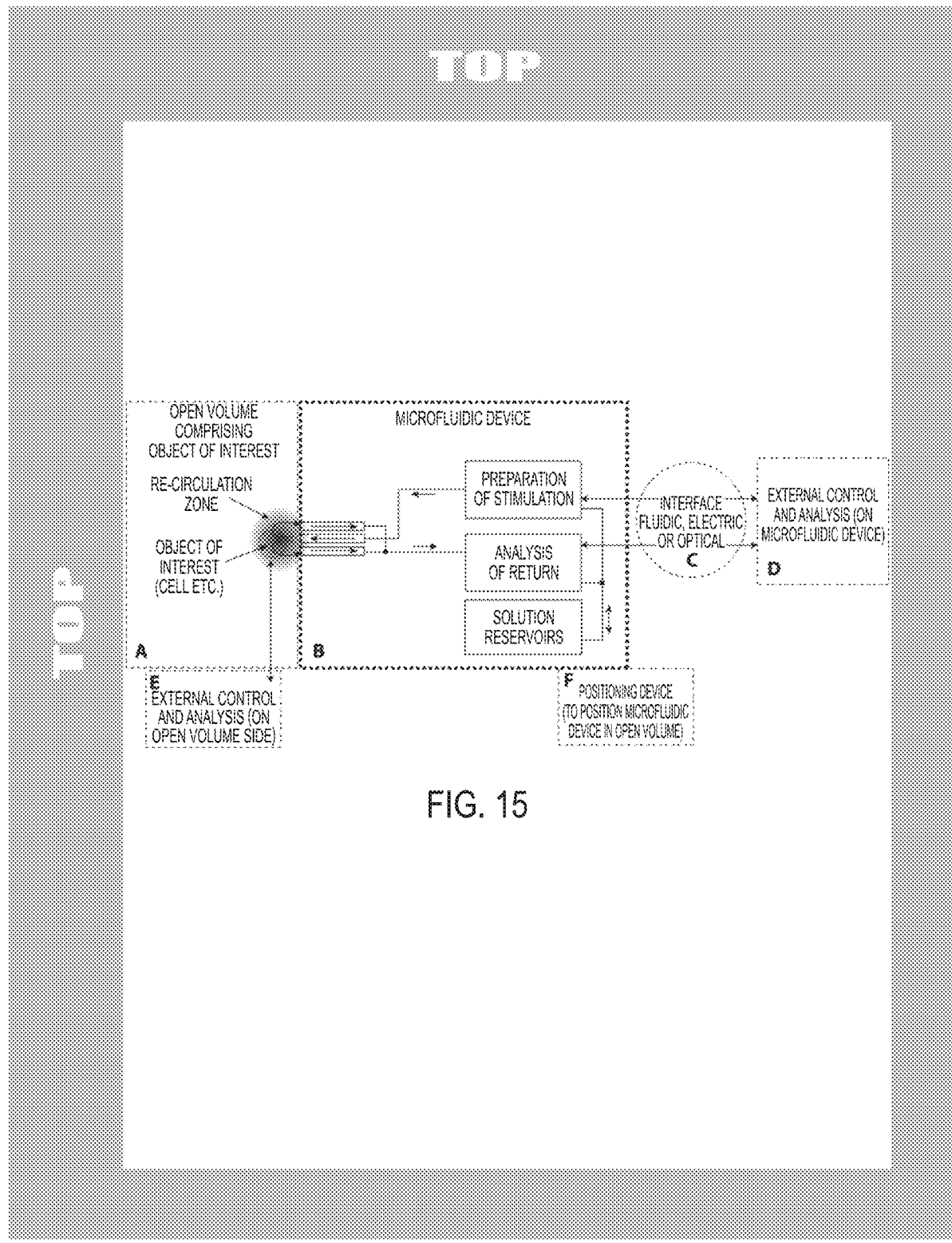
FIG. 15 illustrates detailed application concept of the microfluidic pipette according to preferred embodiments of the present invention. Panel A shows an open volume (reservoir) comprising the object of interest and recirculation zone(s). Panel B shows a microfluidic core device with specific functionality. Panel C shows and interface to external pipette controls. Panel D shows external pipette control. Panel E shows open volume side control. Panel F shows pipette positioning.

According to further preferred embodiments and as shown, for example, in FIG. 15, a generic application concept of the microfluidic pipette is depicted, using in a non-limiting way six different component groups. Preferably, the open volume comprises the objects of interest, such as sensors, cells or surface-embedded elements or combinations of them (FIG. 15, Panel A). Preferably, the open volume further comprises the recirculation zone or a concentration gradient constructed from multiple recirculation zones (FIG. 14). In further preferred embodiments, the open volume preferably interfaces to the microfluidic device, which contains the specific core functionality of the pipette (FIG. 15, Panel B). Preferably, channel exits define the interface of the pipette to the open volume. Examples for core functions include, but are not limited only to, gradient generation, fluid multiplexing, dilution, on-chip analysis, control electrodes. Preferably, the microfluidic device also interfaces to the external pipette control. Preferably, this can be achieved by electrical wires, fluid or gas pressure conduits or optical fibres, electromagnetic, piezoelectric or mechanical control elements (FIG. 15, Panel C). Further, the control-interface is suitably terminated by the external pipette control, exercising the appropriate steering, and regulation of pipette function and recirculation zone(s) (FIG. 15, Panel D). Further control elements can be suitably positioned depending on the desired application.

In one exemplary embodiment, such control element comprises a reservoir side control, such as manipulation and positioning of sensors, temperature control, imaging devices, optical fibers. In another embodiment, such a control element preferably comprises pipette positioning, which can preferably be achieved by micromanipulation or micropositioning.

Figure 16:
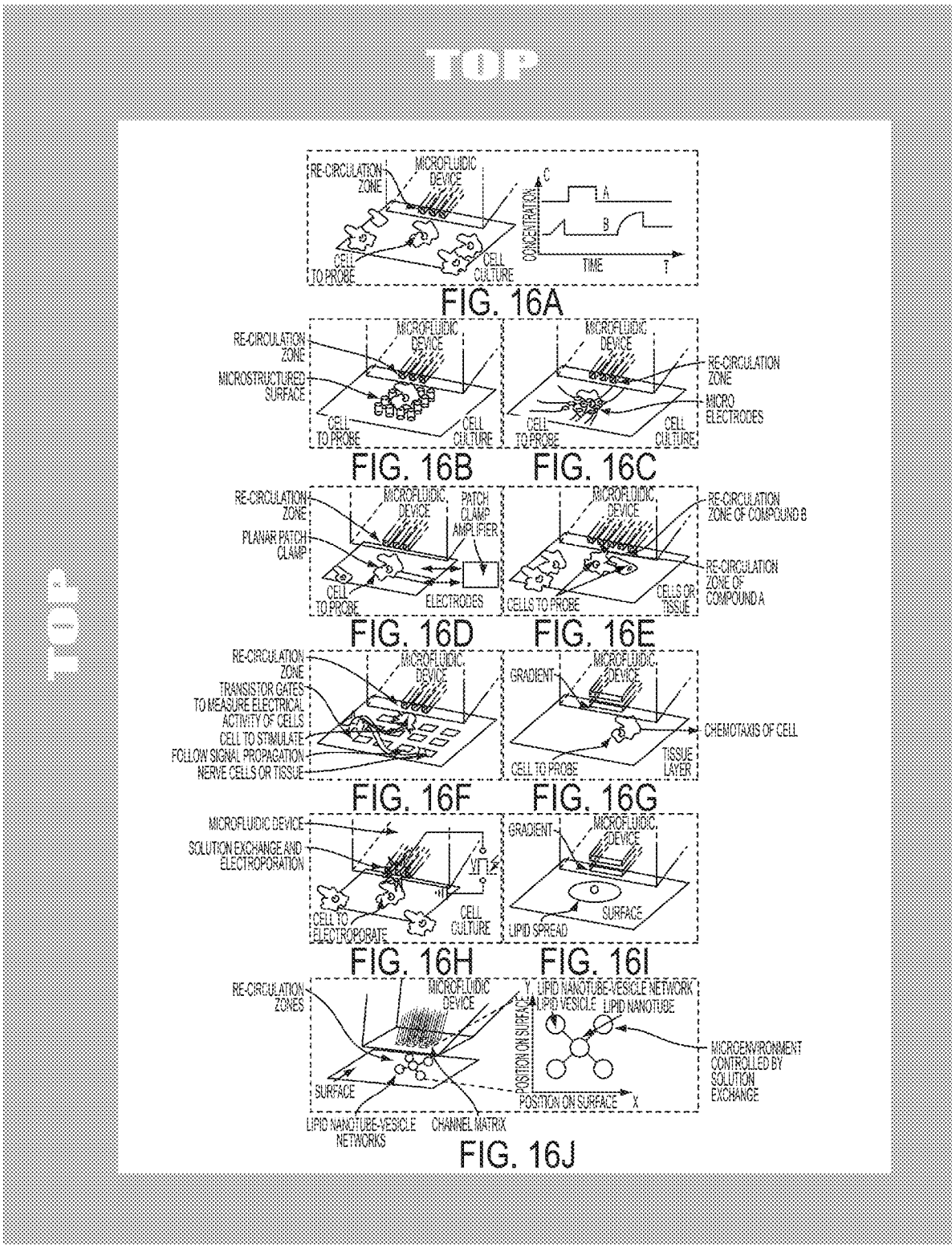
FIGS. 16A-16J are exemplary illustrations involving single or multiple cells that are exposed to one or more recirculation zones. Other cells that are not in the recirculation zones will not be significantly affected, even though they are present in the same open volume.

Several preferred embodiments of applications are depicted in FIG. 16.

Non-limiting application examples include single or multiple cells that are exposed to one or more recirculation zones. Preferably, other cells that are not in the recirculation zones will not be affected, even though they are present in the same open volume. Recirculation efficiently removes all flow components, that are present in the recirculation zone, from the open volume, thus avoiding contamination of the open volume.

According to further exemplary embodiments and as shown in FIGS. 16A-16J, FIG. 16A illustrates solution exchange around a single cell immobilised on planar surface. Preferably, the cell is exposed to pulsed or continuous chemical stimuli, by e.g., a receptor ligand, exclusively inside the recirculation zone. According to further preferred embodiments, one important adjustable parameter when applying such chemical stimuli is stimulant concentration. Concentrations of fluid components inside the recirculation zone can be suitably altered in a non-limiting fashion by means of on-device diluters, mixers or multiplexers. Preferably, the flow shear and exposure area can be adjusted by adjusting the rates of the inflow and outflow channels appropriately, reducing or increasing the volume of the recirculation zone and simultaneously controlling the magnitude of shear forces exerted on the cell by flow. Examples of device use include, but are not limited only to, studies of cellular regulatory mechanisms involving gene-expression, ion-channels, receptors and enzymes, where the cell of interest to be subjected to the recirculation can be freely chosen, as well as time-dependent stimulation protocols, which would then allow it to trigger chemical reactions.

Reaction products can in one embodiment be monitored in the open volume in a non-limiting fashion via fluorescence imaging, electrical probing with patch-pipette or microelectrodes. Alternatively, products can in another embodiment be recirculated into the microfluidic device and are processed, analyzed or monitored there. For example release of neurotransmitters from nerve cells can be sampled and studied as a function of receptor stimulation.

In another embodiment, cells or sensors can be suitably immobilized on patterned or structured surfaces, where the structures can preferably be chemical or two-dimensional (e.g., thin self-assembled monolayers with different properties stamped on surfaces), three-dimensional geometrical (e.g., micromolded structures, photoresist or polymer structures, lithographically patterned metals, lithographically patterned oxides, and the like) as depicted in FIG. 16B. This enables studies of combined effects of structure (such as confinement) and chemical stimulation. In another embodiment, microstructures also serve as sensory parts like microdynamometers, microelectrodes (FIG. 16C), or optical sensors (surface plasmon resonance).

In another embodiment, solution exchange is applied around a single cell immobilised on a planar surface and connected to a planar patch-clamp device (FIG. 16D). Preferably, multiple recirculation zones are used to simultaneously change the solution environment around multiple target objects, such as cells (FIG. 16E). These objects of interest are co-immobilised on a planar surface in appropriate distance to each other, matching the position of the recirculation zones. On more complexly structured surfaces, e.g., featuring CMOS sensor elements, stimulation of localized parts of a cell-network, such as a neuronal cell network, can be suitably achieved with the microfluidic pipette, while a direct response from different parts of the network is monitored by means of the surface embedded sensor-elements. In another exemplary embodiment, chemotaxis of loosely surface-attached cells is caused by a concentration gradient. In one exemplary embodiment, the gradient is suitably generated by a series of interconnected recirculation zones, and it can be manipulated towards or away from the cell.

In another embodiment, surface-immobilized single cells or vesicles can be electroporated using an electrical field generated by means of electrode pairs embedded in the pipette. Short electrical pulses are suitably applied through the channel exits, leading to field strengths of 100-400 V/cm in the recirculation zone, which is the field strength required for electroporation. In this non-limiting example, the field is localized around the object of interest, while other objects in the shared open volume are subjected to only considerably lower electrical field strengths, which do not lead to membrane electroporation.

In another embodiment, two-dimensional molecular films on planar surfaces are brought in contact with the recirculation zone. In another further exemplary embodiment, the recirculation zone carries $Ca^{2+}$ ions, and the molecular film consists of phospholipid layers, which exhibit migration (spreading) along a $Ca^{2+}$ concentration gradient towards the recirculation zone, following an artificial chemotaxis scheme.

In another embodiment, multiple fluid components in multiple independent, closely spaced recirculation zones, target simultaneously different nodes in a surface-immobilized vesicle nanotube network or of a biological cell-network such as a neuronal network. The multiple fluid components can preferably be composed of a single active chemical compound, that is applied in different concentrations, or as different active chemical compounds present in the same or different concentrations. Application examples A-J are non-limiting, other applications where single or multiple chemical microenvironments around surface-immobilized or droplet-confined objects of interest are required, are conceivable.

Figure 24A:
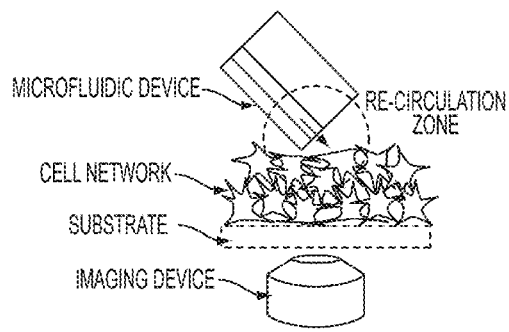
FIGS. 24A-24C show stimulation of localized parts of a cell-network, such as a neuronal cell network.
Figure 24B:
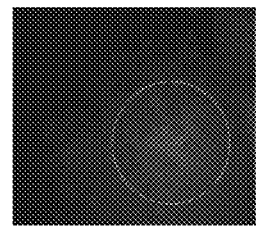
Figure 24C:
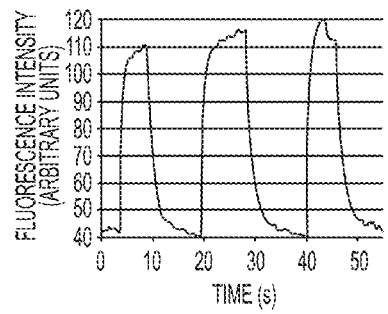

In a preferred embodiment, parts of a cell network can be stimulated (FIG. 24). In this embodiment microfluidic device is positioned in the vicinity of a biological tissue culture of a cell network which is thereby penetrated by the recirculation zone.

Figure 23:
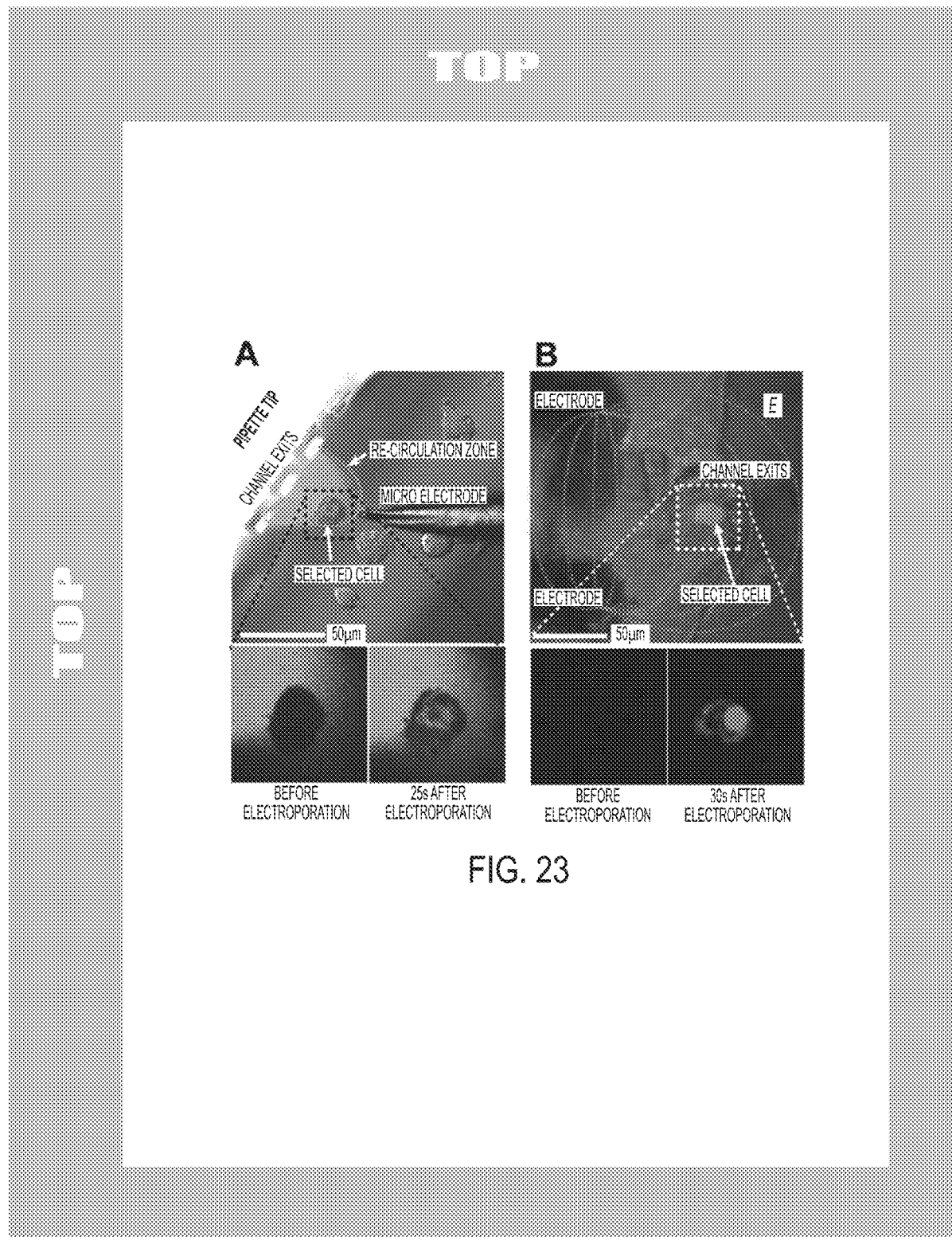
FIG. 23 shows confocal fluorescence and bright field microscopy overlay images, demonstrating the combination of the recirculation zone with an electroporation setup. Panel A shows an adherent single NG-15 cell in the recirculation of fluorescein in the vicinity of a microelectrode. The cell is loaded with the dye only after an electrical pulse is applied. Panel B shows an adherent single NG-15 cell in the recirculation of YO-PRO-1. In this example, the electrodes are attached to the microfluidic device. The cell is loaded with the dye only after electrical pulse is applied. YO-PRO-1 is a non-fluorescent material which becomes fluorescent only upon binding to DNA, therefore the cell nucleus shows particularly bright fluorescence.

In an additional embodiment the recirculation zone can be applied to electroporate biological or artificial cells (FIG. 23, Panels A and B). In this embodiment, an electrode is placed in the vicinity of cells in a recirculation zone. Cells are loaded by the application of an electrical pulse.

Figure 17:
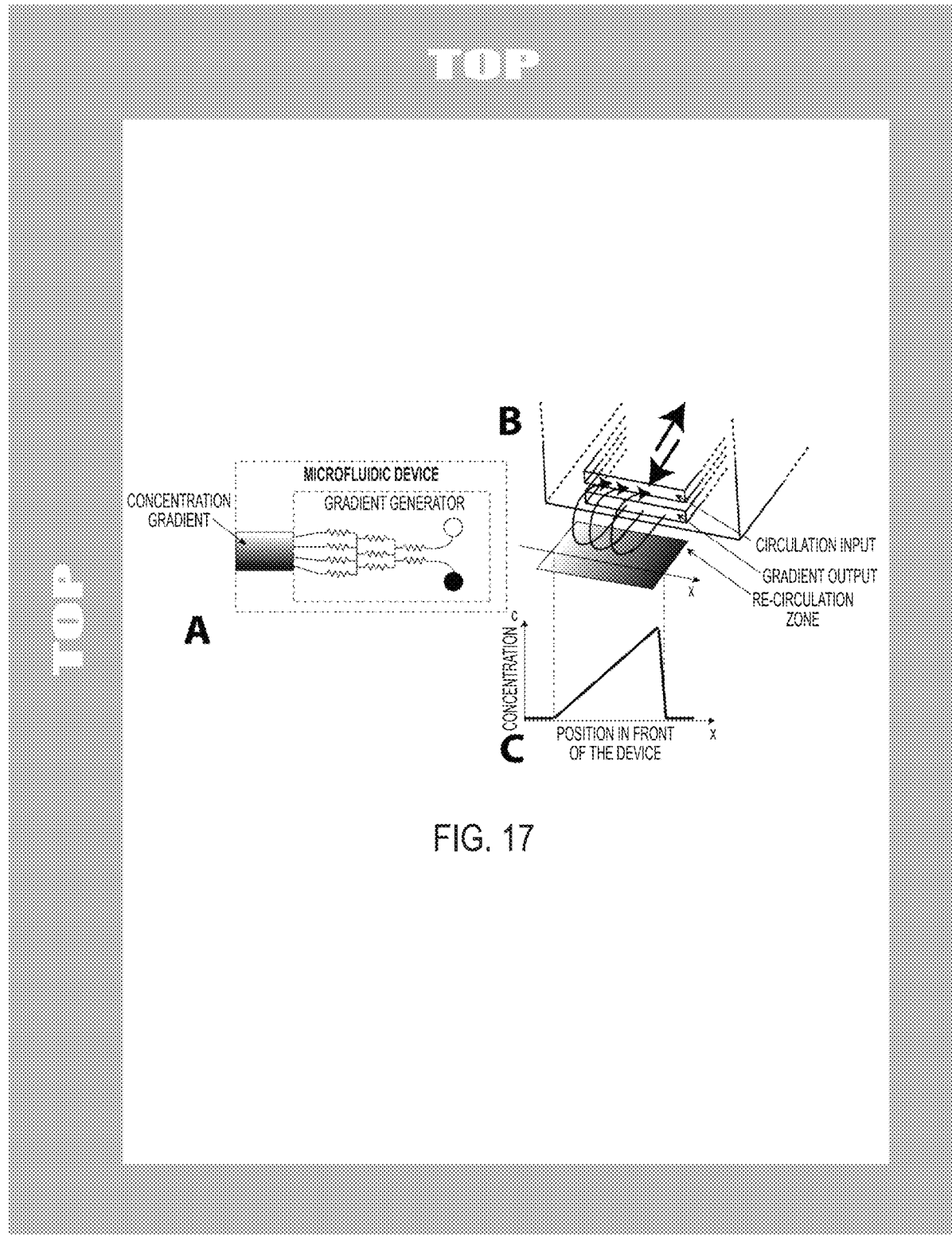
FIG. 17 illustrates the generation of complex chemical environments. Panel A shows an example of on-chip gradient generation by means of gradient generator network and attached diffusional mixer. Panel B shows broad recirculation zone with concentration gradient along one axis. Panel C shows a concentration gradient profile.

In certain embodiments, complex chemical environments can be generated. An example of a complex chemical environment is one having a concentration gradient of a chemical. For example, an on-chip gradient can be generated by means of a gradient generator network attached to a diffusional mixer (FIG. 17, Panel A). In another example, a broad recirculation zone can be generated having a concentration gradient along one axis (FIG. 17, Panels B and C).

Figure 18:
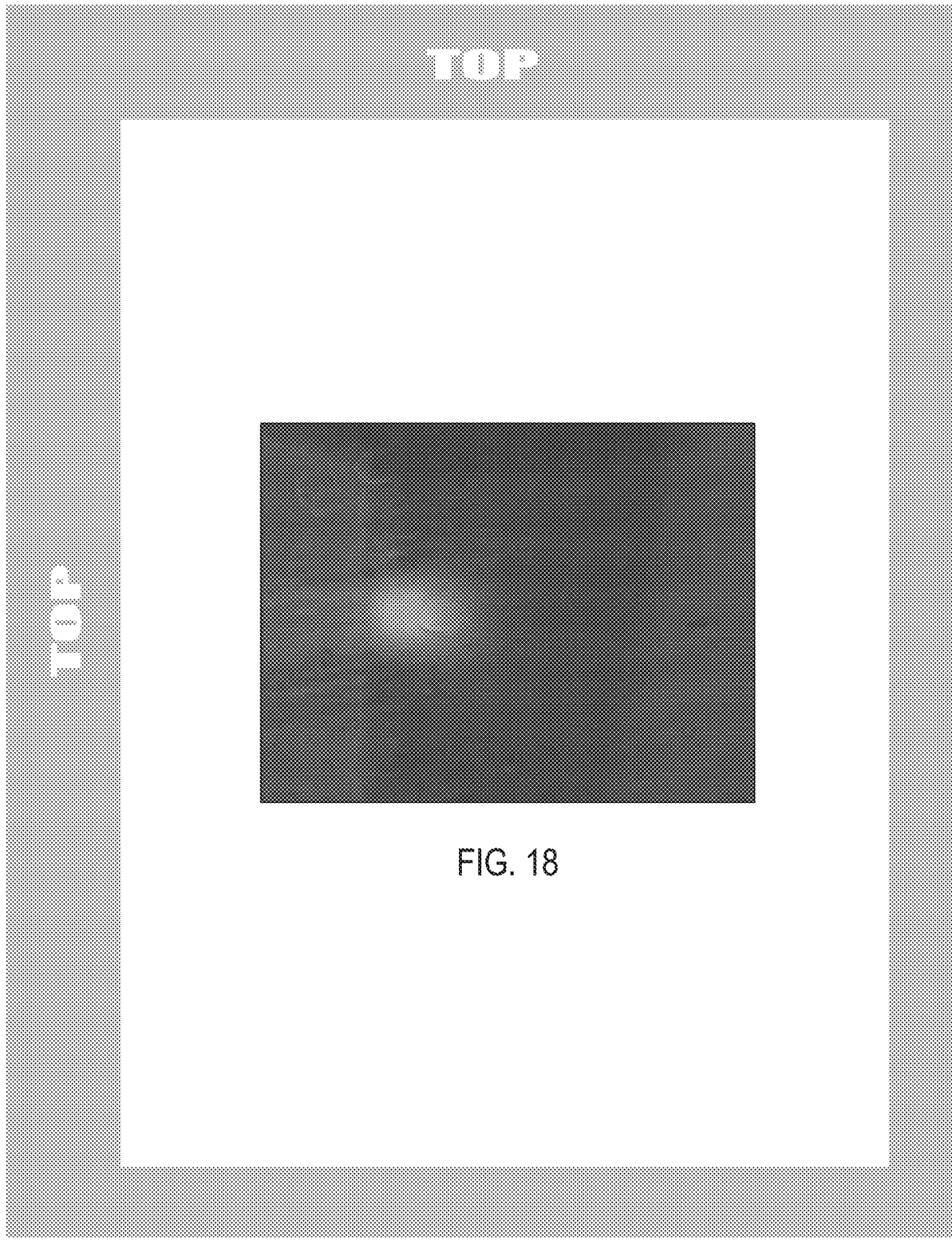
FIG. 18 illustrates an example of solution exchange around single cell visualized with flourscene containing solution under an inverted microscope with combined brightfield and fluorescent lamp illumination. The diameter of the recirculation zone is approximately 30 µm.

According to further exemplary embodiments, more complex continuos recirculation microenvironments, such as linear and non-linear concentration gradients, are easily achieved by combining individual recirculation zones (FIG. 18). They offer the possibility to expose multiple objects of interest to exactly defined concentration ratios simultaneously. Preferably, a diffusional mixer, essentially a broad channel of defined length, is placed in front of the combined channel outlets (FIG. 18A). Preferably, a broad combined recirculation zone is generated at the end of the mixer (FIG. 18B), allowing exactly defined gradients (FIG. 18C).

The following Examples are offered by way of illustration and not by way of limiting the remaining disclosure.

Materials

Two-inch n-type silicon wafers, photoresist MICRO-CHEM™ SU8-10, and SU8 developer were provided by the MC2 cleanroom facility at Chalmers University of Technology of Göteborg, Sweden. A DOW CORNING® SYLGARD® 184 PDMS kit was obtained from GA Lindberg of Göteborg, Sweden. Dichlorodimethylsilane, fluorescein disodium salt, and blasticidin were obtained from Sigma-Aldrich Corp. of St. Louis, Mo. Cell culturing medium DMEM/F12 with glutamine, fetal calf serum and ACCUTASE® cell detachment solution were obtained from PAA, Pasching, Austria. ZEOCIN™ selection antibiotic was obtained from Invitrogen, Carlsbad, Calif. All solutions used in the study were prepared in MILLI-Q® grade deionized water. PTFE tubing was obtained from VWR, Radnor, Pa. Electronic components were ordered from ELFA A.B. or Farnell A.B in Sweden.

Device Fabrication

All molds for replica molding were prepared in the ISO100 clean room facility MC2 at Chalmers University of Technology. PDMS casting and curing was carried out in ambient environment in a standard laboratory. The layout was designed in Autodesk AutoCAD 2008. Patterns for each layer were transferred to the E-beam lithography system JEOL JBX-9300FS and written to chromium coated soda-lime glass masks. Wafers were treated before use by means of oxygen plasma in the microwave plasma processor Tepla 300PC (1 mbar, 250 W for 1 min, $O_2$ gas flow 400 sccm).

Resists were exposed on a Karl Süss MA6 contact mask aligner (G-line, 5-6 mW/cm$^2$). For the mold, SU8-10 was spin-coated at 3000 rpm for 30 second, soft baked at 65° C. for 2 minute, ramped to 95° C., baked for 5 minutes (all on a hot plate), and left to cool to room temperature.

Subsequently, the wafers were exposed with 5 mW/cm$^2$ UV-Light for 20 seconds through a dark field mask, post-baked for 1 minute at 65° C., ramped to 95° C., baked for 2 minutes, and finally left to cool to RT. The resist was developed in SU8 developer for 2 minutes, rinsed with developer, and washed in de-ionized water (DIW). The mold was blow-dried and cleaned in oxygen plasma (50 W, 250 mTorr, 1 min).

The mold was hard-baked at 200° C. (air circulation oven) for 30 minutes, with slow heating and cooling. The geometries of the moulds were characterized with an Olympus MX40 microscope and a stylus profiler Tencor AS500. (The channel height was 10 µm.) Before use, the mold and a clean silicon wafer were anti-adhesion-treated with dichloro dimethyl silane by exposing the surfaces to the vapors under a Petri dish cover for 5 minutes. PDMS pre-polymer was prepared by mixing parts A and B in a ratio 10:1 and degassed for 15 minutes in a desiccator.

Subsequently, the mold was used to cast a PDMS slab. PDMS slabs of a thickness greater than 2 mm were cast using a molding template around the wafer. Thinner slabs were prepared directly on the wafer by self-spreading (~1-2 mm) or spin-coating (<1 mm). For the thin membranes, PDMS was spin-coated onto the clean wafer, using spin parameters listed in Table 1. PDMS structures were cured at 95° C. (air circulation oven) for 1 hour. Thereafter the chip was assembled by oxygen plasma bonding in a Plasma Therm Batchtop PE/RIE at 250 mTorr, 85 W, 10 sccm $O_2$ for 10 seconds.

First, the bottom surface of the thick PDMS slab and the thin PDMS membrane, still adhered to the wafer, were treated, aligned and bonded at 95° C. (air circulation oven) for 1 hour. Then the composite (1) was peeled off and 1 mm diameter holes were punched through the slab (2). The pipette tip was then shaped by means of a sharp cutter (3). The composite slab and a glass coverslip were plasma treated and bonded together, an overhang of 5 mm with respect to the glass slide edge was left (4). Finally, the chip was left to bond completely overnight, reproducibly yielding a functional device (FIG. 1B, numbers (1)-(4) above refer to this figure).

Table 1, shown below, shows spin coating parameters for PDMS membrane fabrication.

TABLE 1

Spin coating parameters for PDMS membrane fabrication

| Rotation speed (rpm) | Spin time (s) | Membrane thickness (µm) |
|---|---|---|
| 1500 | 60 | 40 |
| 2000 | 300 | 12 |
| 2500 | 600 | 7 |

Interface

The PDMS-glass composite was interfaced with pressure lines by two different non-limiting means: thin devices were clamped with a soft-material gasket manifold, covering and sealing the channel entrances, while thick devices were interfaced by tubing anchored in the PDMS (shown in FIG. 1B). Driving pressures are generated by external pumps and electronic valves or alternatively by on-chip micropumps and microvalves.

Micromanipulation

A non-limiting means of micropositioning is the application of water hydraulic micromanipulators (Narishige MH-5, Japan), which allows 3D-positioning of the pipette, bringing the recirculation zone into proximity of the desired object of interest.

Cell Culture

Adherent T-REx-CHO cells expressing the human TRPV1 protein were cultivated in Petri dishes for 2-6 days in culture medium (DMEM/F12 with glutamine) supplemented with fetal calf serum (10%), zeocin (350 µg/ml) and blasticidin (5 µg/ml). 18-24 hours prior to experiments, the cells were incubated in DMEM/F12 medium with glutamine, supplemented with fetal calf serum (10%) and doxycycline (1 µg/ml) in order to induce expression of the TRPV1 protein. Before the experiments, cells were washed with extracellular buffer (see below) and incubated for 5 minutes with Accutase® at 37° C.

Solution Exchange—Electrophysiology

Figure 20:
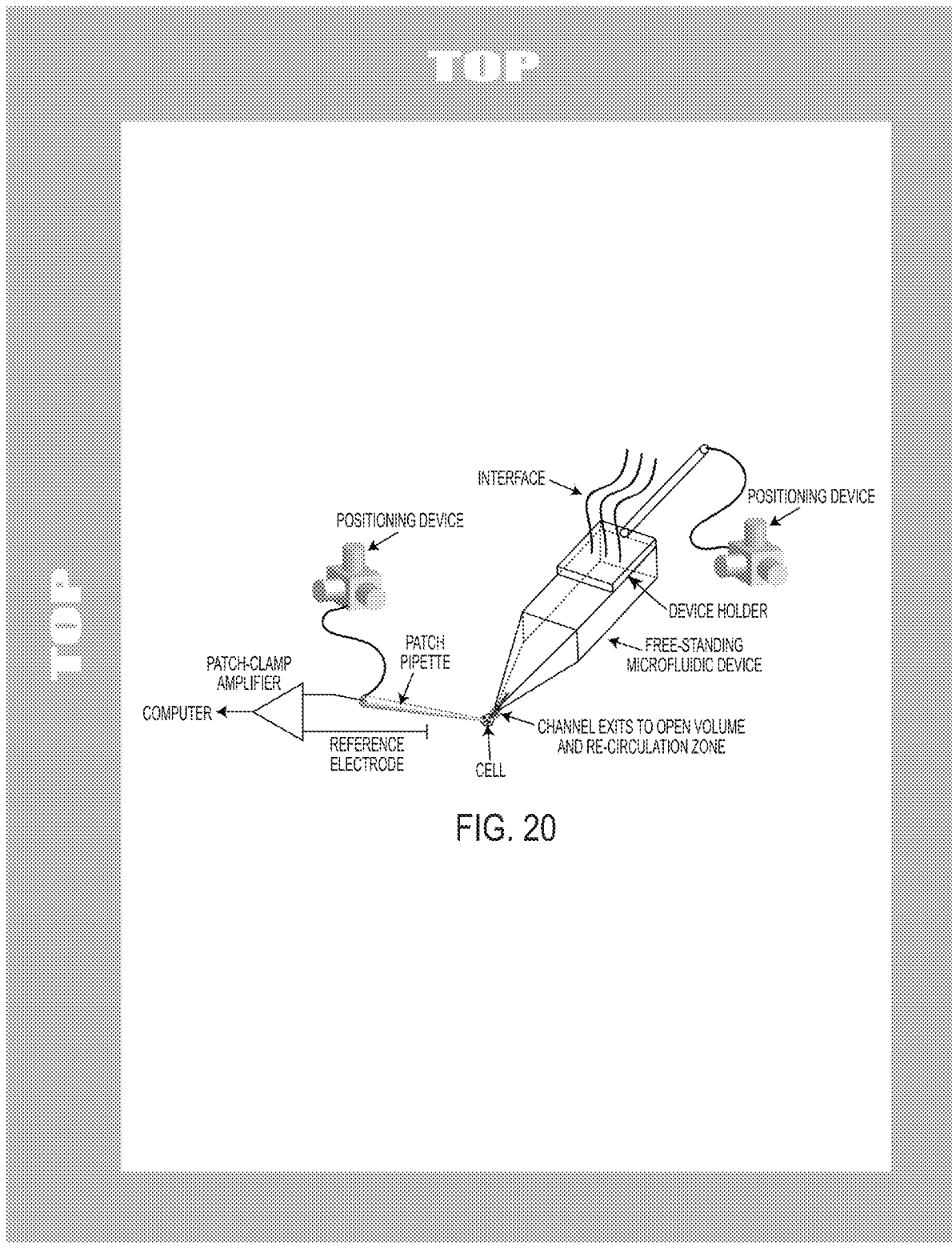
FIG. 20 shows solution exchange around single cells. This figure illustrates the solution exchange applied in electrophysiology (patch clamp) drug response measurement using single cells.
Figure 21:
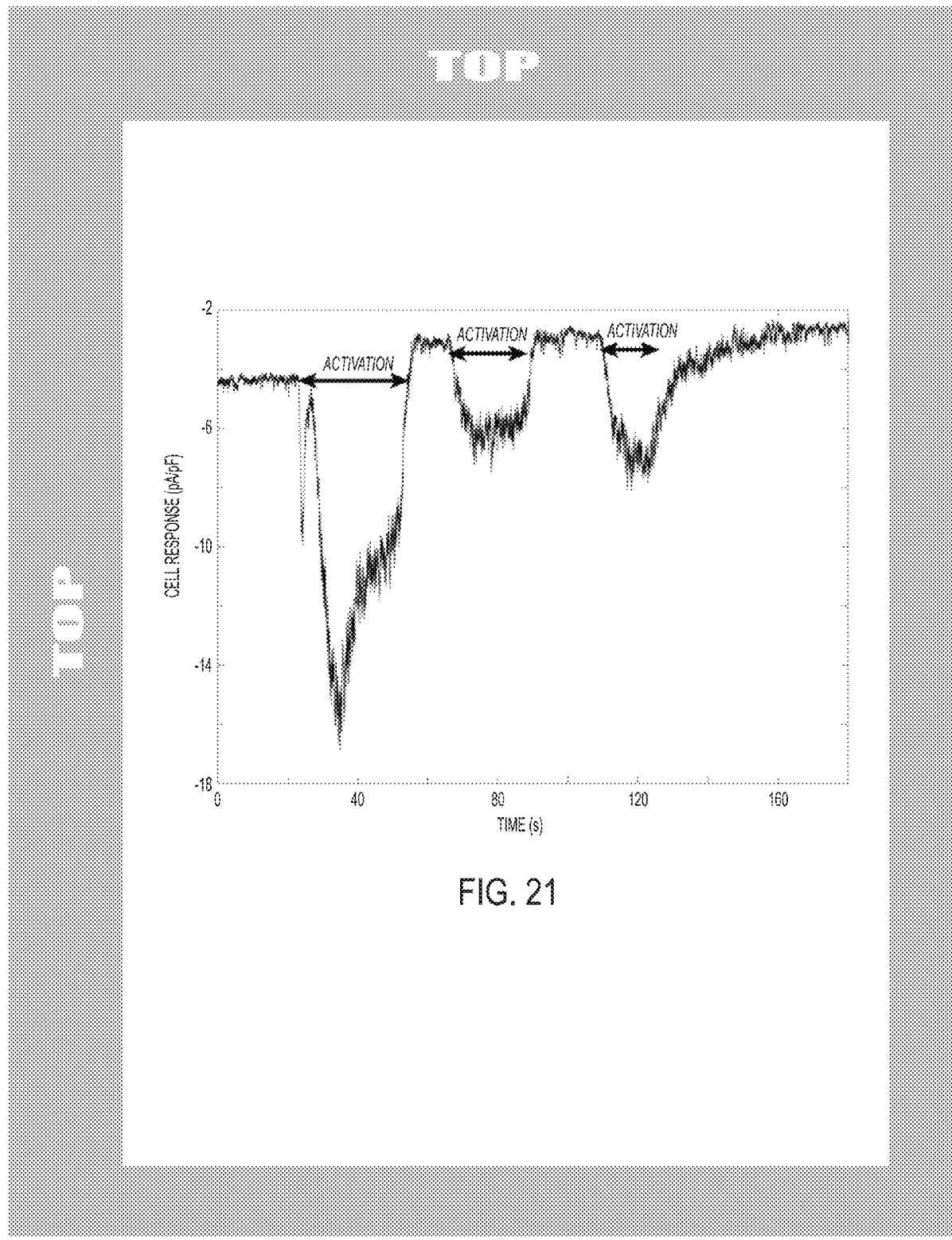
FIG. 21 shows the electrophysiological response of a cell expressing hTRPV1 ion-channels, which are activated by an acidic agonist (extracellular buffer pH 5.5). Stimulation of the cell was switched on and off by adjusting the inflow/outflow ratios and consequently changing the size of the recirculation zone, or by micromanipulating the channel exits of the free-standing microfluidic device towards or away from the cell.

The whole cell patch-clamp methods were used in all experiments. Patch pipettes were pulled with laser based pipette puller P-2000 by Sutter Instruments Co., California, USA. The resistances of the pulled patch pipettes were 2-10 MΩ. All data were recorded using a HEKA EPC10 patch-clamp amplifier with Patchmaster software (HEKA Elektronik, Germany). The cells were clamped at −60 mV and series resistance compensation was performed to 80%. Current signals were recorded at a sampling frequency of 5 kHz and low pass filtered at 1 kHz. The cell bath solution (extracellular buffer) contained (in mM), 140 NaCl, 5 KCl, 1 $CaCl_2$, 1 $MgCl_2$, 10 Hepes, 10 D-glucose; pH was adjusted to 7.4 with NaOH. The patch-clamp electrode solution (intracellular buffer) contained (in mM) 120 KCl, 1 $CaCl_2$, 2 $MgCl_2$, 11 EGTA, and 10 HEPES; pH was adjusted to 7.2 with KOH. For pH stimulations, the pH of the extracellular solution was set to 5.5, using HCl or NaOH. (FIG. 21). For the solution exchange either pipette was moved with micromanipulator or solution was exchanged by on-chip switching. (FIG. 20). Flow rates were in the range of 1-5 mm/s.

Solution Exchange—Cytology (Blebbing)

Figure 19:
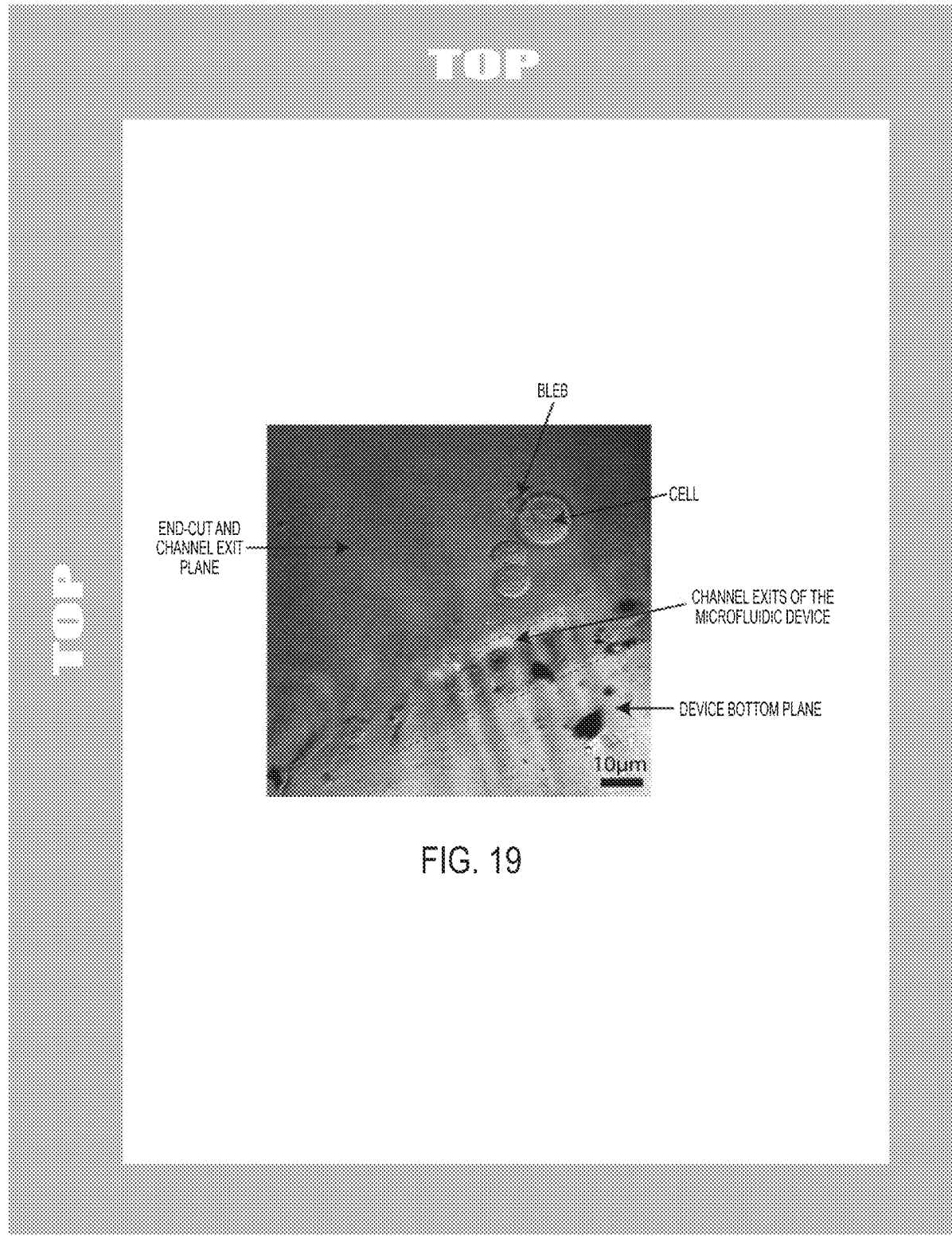
FIG. 19 shows localized cell blebbing at pipette outlet. The recirculation zone carries 25 mM formaldehyde and 2 mM DTT in a HEPES buffer.

The culturing medium was removed, and the cells were washed twice with HEPES buffer, containing 140 mM NaCl, 1 mM $CaCl_2$, 5 mM KCl, 1 mM $MgCl_2$, 10 mM d-glucose, and 10 mM HEPES at pH 7.4. Afterwards the cells were covered with 2 mL HEPES buffer, and the dish was placed on a confocal microscope stage. The pipette was loaded with blebbing solution, containing 25 mM formaldehyde, 20 mM DTT, 2 mM $CaCl_2$, 10 mM HEPES, 0.15 M NaCl at pH 7.4, and 10 µM fluorescein for fluorescence monitoring purposes. After placing the pipette into the open volume, it was aligned to surface immobilized single cells or cell groups. (FIG. 19). Fluorescein emission was used to control the size and shape of the recirculation zone to completely cover the cells, but not the environment around them. The cells were exposed to the recirculation zone for 15 minutes, and growth of membrane blebs was recorded. Control recordings were carried out outside the recirculation zone, confirming that no blebbing occurred on these unexposed cells. Several successive experiments were carried out in the same open volume, confirming the absence of contamination from the pipette.

Example Device

Figure 22:
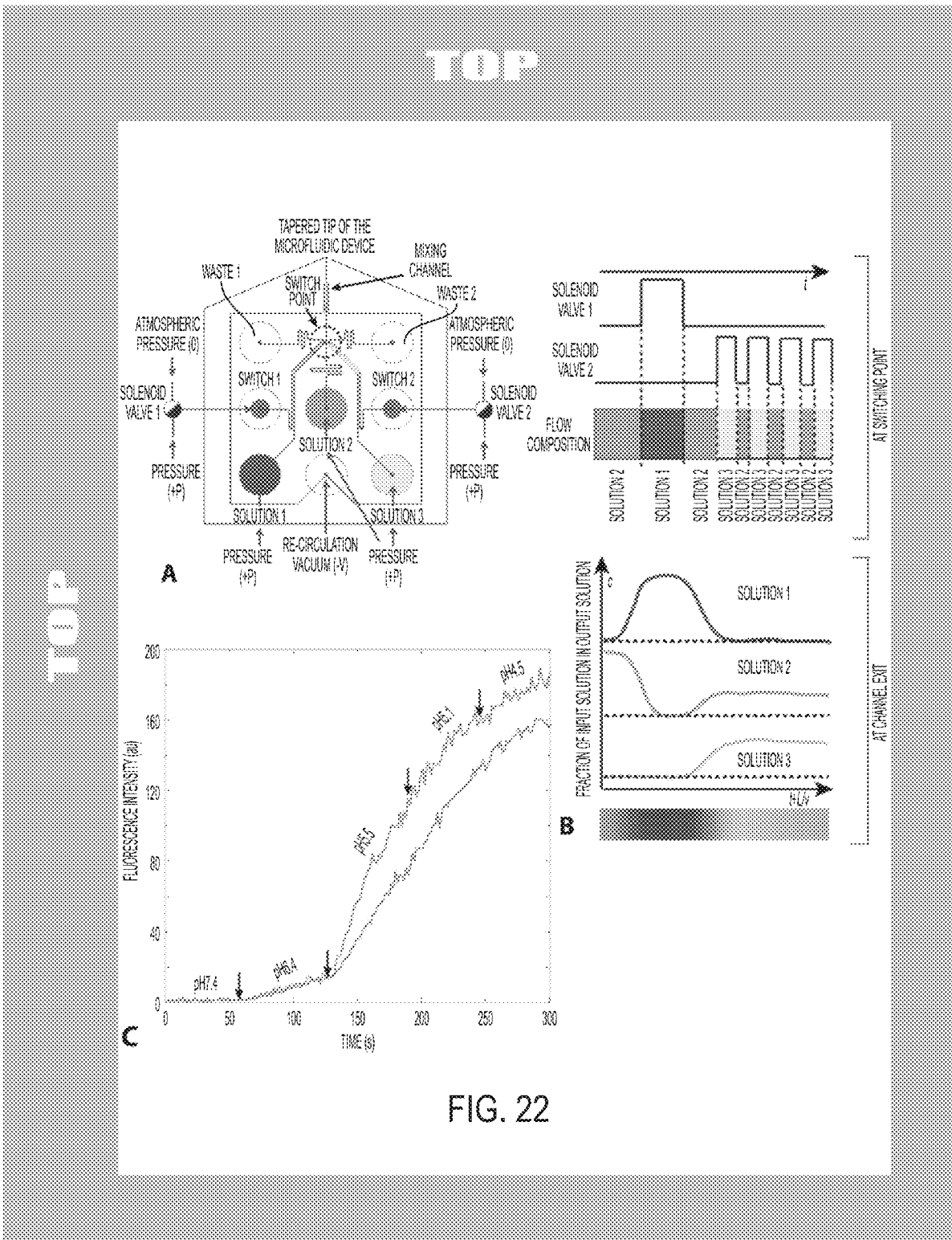
FIG. 22 shows an example design and an application example of a microfluidic device. This example device is capable of changing the composition of the recirculation zone over time by multiplexing between several liquid inputs. Panel A is a diagram of the layout of the device. Channel exits are located at the tapered tip of the microfluidic device to facilitate applicability. The device interface contains three solution inputs (marked as solutions 1, 2 and 3), two switching controls (marked as switches 1 and 2) two waste outputs (marked as wastes 1 and 2) and one recirculation output. The flow is pressure driven. All solution inputs are pressured at pressure +P, while switching controls can be pressurized to the same pressure (+P) or to the atmospheric pressure (0). The switching determines which of the three solutions is directed towards the channel exit. Switching point and channel exit are separated by a mixing channel. Panel B is a set of graphs illustrating the propagation of concentration pulses of the three input solutions through the mixing channel. Short pulses mix almost completely in this channel, where the final composition at the channel exit is determined by the duty cycle of the pulse sequence. Panel C is a graph of an application of on-chip dilution of an acidic buffer, to measure simultaneously two single-cell dose-response curves. hTRPV1 ion channel opening in Chinese Hamster Ovary cells was recorded, depending on the on-chip generated temporal pH gradient. The response was measured as fluorescence intensity, depending on the uptake of fluorescent YO-PRO-1 dye through the activated ion channels.

An example of a device capable of changing the composition of the recirculation zone over time by multiplexing between several liquid inputs is shown in FIG. 22, Panel A. Channel exits are located at the tapered tip of the microfluidic device to facilitate applicability. The device interface contains three solution inputs (marked as solutions 1, 2 and 3), two switching controls (marked as switch 1 and 2) two waste outputs (marked as waste 1 and 2) and one recirculation output. (FIG. 22, Panel A) The flow is pressure driven. All solution inputs are pressured at pressure +P, while switching controls can be pressurized to the same pressure (+P) or to the atmospheric pressure (0).

Pressure +P can, in some embodiments, range from about 2 kPa to about 100 kPa. For example, pressure +P can be selected from the group consisting of: between about 2 kPa and about 10 kPa, between about 10 kPa and about 20 kPa, between about 20 kPa and about 30 kPa, between about 30 kPa and about 40 kPa, between about 40 kPa and about 50 kPa, between about 50 kPa and about 60 kPa, between about 60 kPa and about 70 kPa, between about 70 kPa and about 80 kPa, between about 80 kPa and about 90 kPa, and between about 90 kPa and about 100 kPa.

The switching determines which of the three solutions is directed towards the channel exit. Switching point and channel exit are separated by a mixing channel. Propagation of concentration pulses of the three input solutions through the mixing channel.

As depicted in FIG. 22, Panel B, short pulses mix almost completely in this channel, where the final composition at the channel exit is determined by the duty cycle of the pulse sequence. One exemplary application is on-chip dilution of an acidic buffer to measure simultaneously two single-cell dose-response curves.

As depicted in FIG. 22, Panel C, hTRPV1 ion channel opening in Chinese Hamster Ovary cells was recorded, depending on the on-chip generated temporal pH gradient. The response was measured as fluorescence intensity, depending on the uptake of fluorescent YO-PRO-1 dye through the activated ion channels.

Additional Pipette Configurations

Referring now to FIGS. 25A-25D, various aspects of a microfluidic pipette 2500 are described. Pipette 2500 includes an substrate 2502 that defines a microfluidic outlet channel 2504 and two or more microfluidic inlet channels 2506a, 2506b.

As discussed herein, pipette 2500 can include additional channels. For example, the pipette 2500 can include a total of about 10 total outlet and inlet channels. In some embodiments, the number of inlet channels is greater than the number of outlet channels. For example, the ration of inlet to outlet channels can be 1:1, 2:1, 3:1, 4:1, 5:1 and the like.

Channels 2504 and 2506 can, in some embodiments, be parallel to each other as depicted. Channels 2504 and 2506 can have variety of cross-sectional profiles as discussed herein. In the embodiment depicted, channels 2504 and 2506 have square cross-sections with cross-sectional widths $w_O$ and $w_I$ and heights $h_O$ and $h_I$, respectively.

The openings of channels 2504 and 2506 can be positioned in a variety of locations on the dispensing region 2508. In some embodiments, the position of the channels 2504 and 2506 is defined with respect to a cross-sectional dimension of the channels 2504 and/or 2506.

In one embodiment, an inter-channel distance $d_{IC}$ can be between about 1 about about 5 times a cross-sectional dimension of channels 2504 and/or 2506. For example, a ratio of $d_{IC}$ to $w_O$, $w_I$, $h_O$, and/or $h_I$ can be selected from the group consisting of: between about 0.5:1 and about 1:1, between about 1:1 and about 1.5:1, between about 1.5:1 and about 2:1, between about 2:1 and about 2.5:1, between about 2.5:1 and about 3:1, between about 3:1 and about 3.5:1, between about 3.5:1 and about 4:1, between about 4:1 and about 4.5:1, and between about 4.5:1 and about 5:1.

In other embodiments, a distance $d_B$ from the bottom 2510 of the openings to the bottom of the substrate 2502 can be between about 0.5 and about 5 times a cross-sectional dimension of channels 2504 and/or 2506. For example, a ratio of $d_B$ to $w_O$, $w_I$, $h_O$, and/or $h_I$, can be selected from the group consisting of: between about 0.5:1 and about 1:1, between about 1:1 and about 1.5:1, between about 1.5:1 and about 2:1, between about 2:1 and about 2.5:1, between about 2.5:1 and about 3:1, between about 3:1 and about 3.5:1, between about 3.5:1 and about 4:1, between about 4:1 and about 4.5:1, and between about 4.5:1 and about 5:1.

Substrate 2502 can be selected from a variety of materials as discussed herein. In some embodiments, the substrate is an optically transparent material such as glass, polydimethylsiloxane (PDMS), poly(methyl methylacrylate) (PMMA), polyethylene (PE), and the like.

Figure 25D:
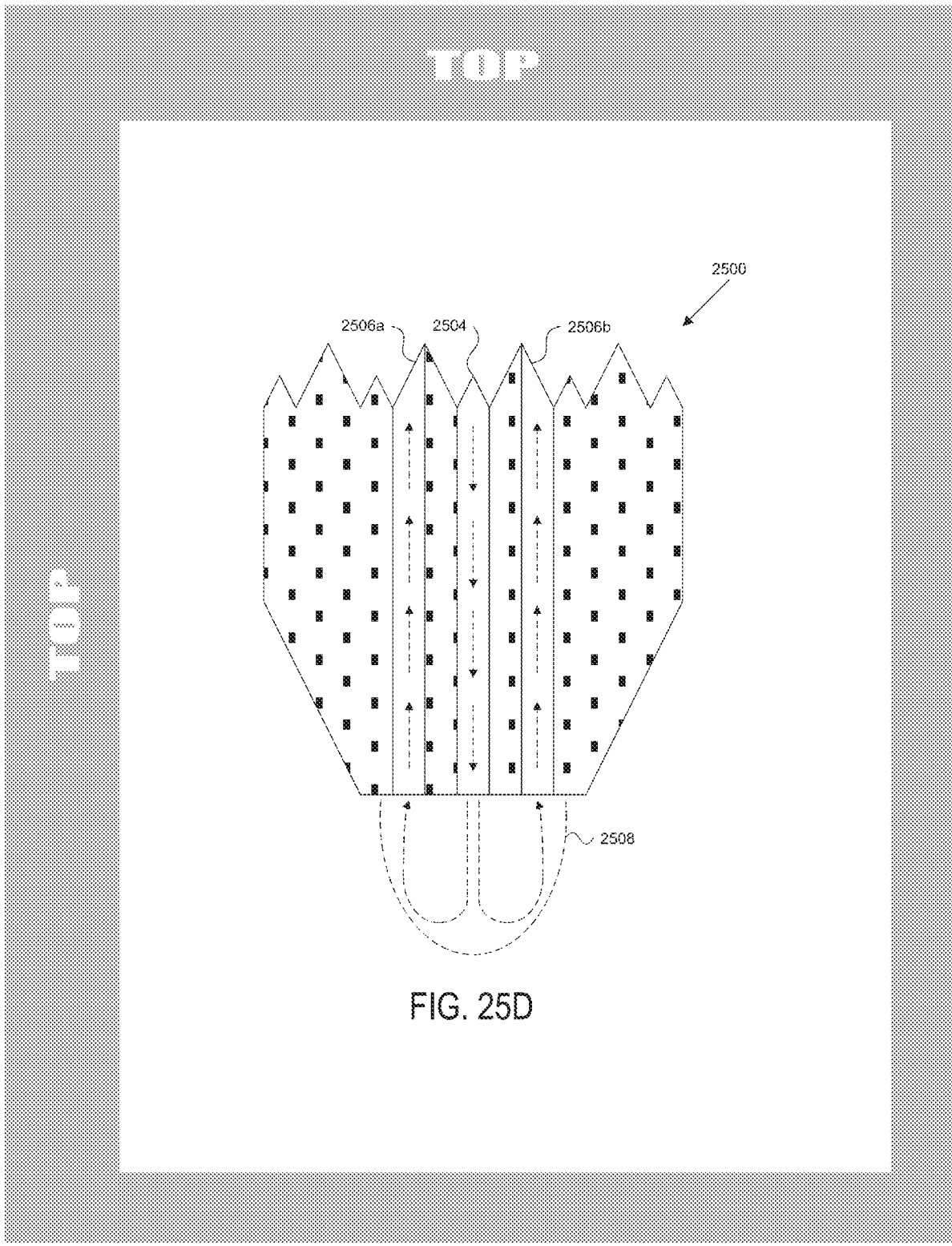

A dispensing region 2508 is located on the exterior of substrate 2502. Each of channels 2504 and 2506 include an opening on the dispensing region 2508. In operation, a fluid flows out of outlet channel 2504 and gathers and circulates in the dispensing region 2508 before being withdrawn by inlet channels 2506. An exemplary flow pattern is depicted in FIG. 25D.

As will be appreciated by one of ordinary skill in the art, the volume and dimensions of the fluid gathered in dispensing region 2508 will vary as a result of a variety of parameters including the ambient pressure in the open volume, the flow rates and pressures in channels 2504 and 2506, the fluid dispensed, the material of substrate 2502, and whether the dispensed fluid is in contact with another object (e.g., a cell). However, the dispensed fluid will often have a generally circular to generally elliptical shape.

The length L of the dispensed liquid can, in some embodiments, be between about 1 and about 10 times the cross-sectional width w of one or more of channels 2504 and/or 2506. For example, the ratio L:w can be selected from the group consisting of between about 1:1 and about 2:1, between about 2:1 and about 3:1, between about 3:1 and about 4:1, between about 4:1 and about 5:1, between about 5:1 and about 6:1, between about 6:1 and about 7:1, between about 7:1 and about 8:1, between about 8:1 and about 9:1, and between about 9:1 and about 10:1.

The width W of the dispensed liquid can, in some embodiments, be between about 1 and about 6 times the cross-sectional width w of one or more channels 2504 and/or 2506. For example, the ratio W:w can be selected from the group consisting of between about 1:1 and about 2:1, between about 2:1 and about 3:1, between about 3:1 and about 4:1, between about 4:1 and about 5:1, and between about 5:1 and about 6:1.

The flow rate through channels 2504 and 2506 can be optimized to achieve a desired result. In general, lower flow rates impose less stress on cells. However, higher flows create a sharper concentration gradient, thereby increasing diffusion into the cell. In one exemplary embodiments having 10 µm square channels, flow rates ranging from 1 nl/second to 10 ml/second were achieved.

Channels 2504 and 2506 can interface with fluid source through a variety of means known to those of skill in the art including male/female connectors, tubing, wells, and the like.

Methods of Stimulating an Object of Interest

Figure 26:
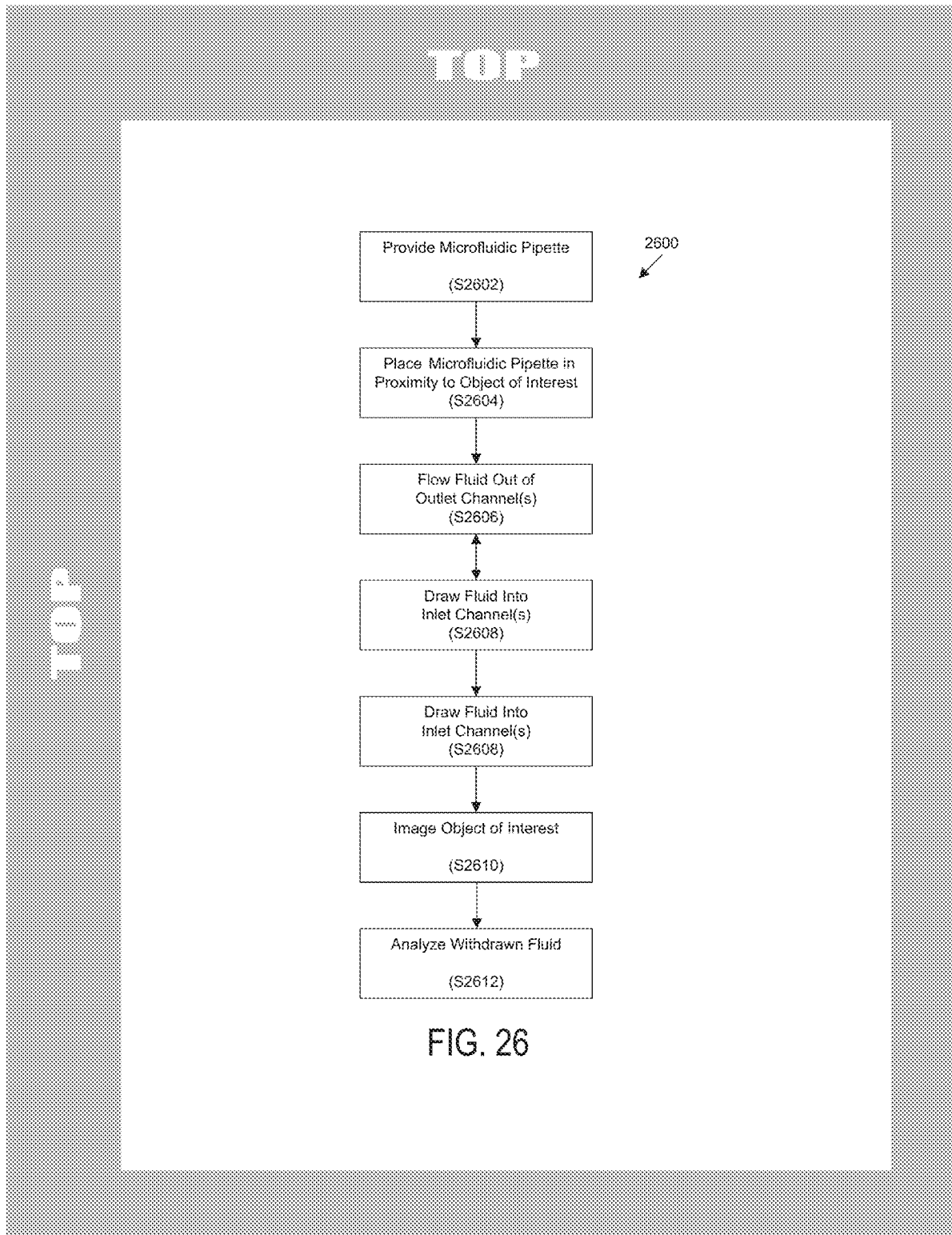
FIG. 26 depicts a method for stimulating an object of interest according to one embodiment of the invention.

Referring now to FIG. 26, a method 2600 of stimulating an object of interest is provided.

In step S2602, a microfluidic pipette is provided. The microfluidic pipette can any pipette as described herein. For example, the microfluidic pipette can have one or more microfluidic outlet channels and one or more microfluidic inlet channels.

In step S2604, the microfluidic pipette is placed in proximity to an object of interest. For example, the microfluidic pipette can be placed lateral to an object of interest. In another object, the microfluidic pipette is positioned at an angle with regard to a horizontal plane. The angle can be selected from a group consisting of: between about 0° and about 5°, between about 5° and about 10°, between about 10° and about 15°, between about 15° and about 20°, between about 20° and about 25°, between about 25° and about 30°, between about 30° and about 35°, between about 35° and about 40°, between about 40° and about 45°, between about 45° and about 50°, between about 50° and about 55°, between about 55° and about 60°, between about 60° and about 65°, between about 65° and about 70°, between about 70° and about 75°, between about 75° and about 80°, between about 80° and about 85°, and between about 85° and about 90°. Such positioning readily allows for observation of the object of interest as discussed herein.

In step S2606, a fluid is caused to flow out of the one or more microfluidic outlet channels. This flow can be implemented though a variety of means including those described herein.

In step S2608, a fluid is caused to flow into of the one or more microfluidic inlet channels. This flow can be implemented though a variety of means including those described herein.

In step S2610, the object of interest is imaged. A variety of imaging devices can be used to image the object of interest including, for example, light microscopy.

In step S2612, the fluid from the microfluidic inlet channels is optionally analyzed, for example, using the devices and techniques described herein.

Flow-Switching

Referring now to FIGS. 27A-27H, the flow-switching embodiments presented herein are further described.

Figures 27A, 27B:
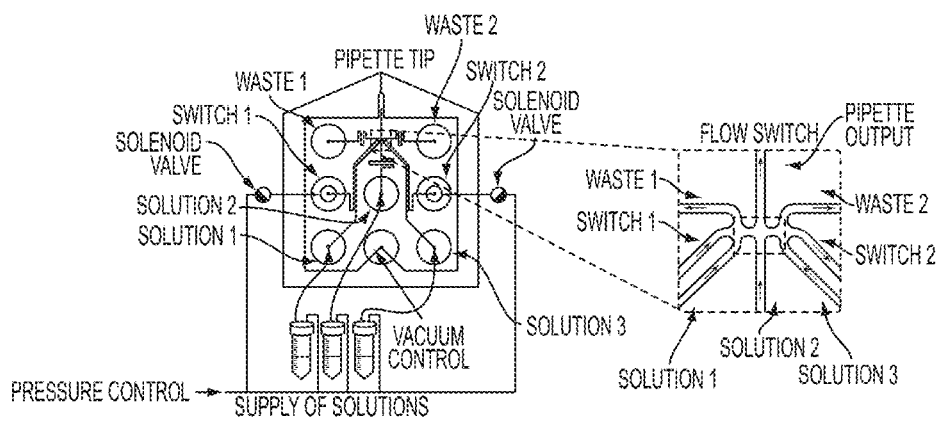
FIGS. 27A-27H provide schematic views of a microfluidic recirculation pipette with embedded three-component flow-switching capability as well as images and graphs demonstrating the operation of the same according to one embodiment of invention.

FIG. 27A provides a schematic view of a microfluidic recirculation pipette with embedded three-component flow-switching capability. The pipette includes a pressure source and a vacuum as well as three solution sources. Switches 1 and 2 regulate the flow of pressure into a switching chamber.

The operation of an eight-channel flow-switching chamber is depicted in FIG. 27B. As clearly seen, switch 2 is actuated to provide atmospheric or negative pressure, each solution is pulled to the right, thereby causing solution 1 to flow to the pipette tip while solution 2 is routed to waste 2 and solution 3 is routed to switch 2. Switches 1 and 2 can be similarly actuated to route solutions 1, 2, 3, or combinations thereof to the pipette tip.

Figure 27C:
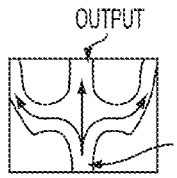
Figure 27D:
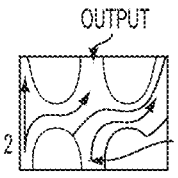
Figure 27E:
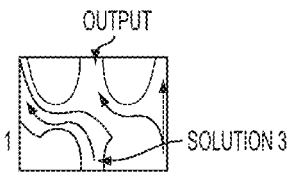

FIGS. 27C-27E are a fluorescence micrograph series depicting the switching between three different solutions. In FIG. 27C, solution 2 is routed to the pipette tip. In FIG. 27D, solution 1 is routed to the pipette tip and solution 2 is routed to waste 2. In FIG. 27E, solution 3 is routed to the pipette tip and solution 1 is routed to waste 1.

Figure 27F:
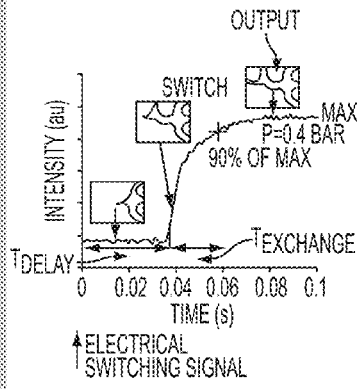

FIG. 27F depicts the typical response characteristics (~50 ms response time as a combination of switching delay and exchange time) of the flow-switching device, measured directly inside the switching node by means of a fluorescein solution.

Figure 27G:
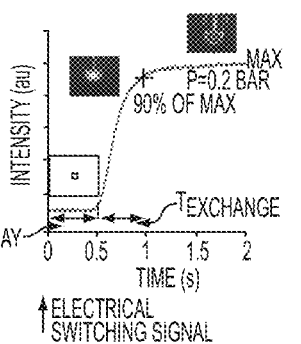

FIG. 27G depicts the typical response characteristics of the flow-recirculation zone. The typical response time for this layout of ~1 s arises from the channel length of the diffusive mixer.

Figure 27H:
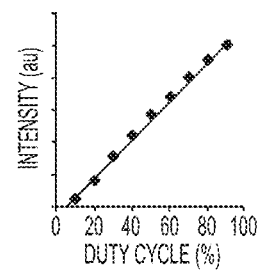

FIG. 27H depicts an on-chip PWFM dilution of a fluorescein-containing buffer depending on the pulsing duty cycle.

The invention claimed is:

1. A system adapted and configured to generate a localized flow circulation zone, the system comprising:
   a free-standing microfluidic pipette comprising three or more channels with exits separated from each other by an outer surface of the pipette;
   a controller programmed to control fluid flows through each of the three or more channels to generate a localized recirculating fluid flow path outside the pipette, wherein:
   (a) liquid leaving the microfluidic pipette through at least one outlet channel exit is withdrawn through at least two inlet channel exits; and (b):
(i) a ratio of inlet channel exits to outlet channel exits in the microfluidic pipette is greater than 1:1 or
(ii) a total cross-sectional area of the at least two inlet channel exits is greater than a total cross-sectional area of the at least one outlet channel exit; and
one or more electrodes adapted and configured to be in communication with fluid in one or more of the three or more channels or the localized recirculating fluid flow path.

2. The system of claim 1, wherein the one or more electrodes are adapted and configured to electroporate an object of interest.

3. The system of claim 1, wherein the one or more electrodes are located on a microelectrode surface.

4. The system of claim 1, wherein the one or more electrodes are embedded in the free-standing microfluidic pipette.

5. The system of claim 1, wherein the one or more electrodes are positioned to be in communication with fluid in one or more of the three or more channels.

6. The system of claim 1, wherein the free-standing microfluidic pipette is adapted and configured to collect fluid from the at least two inlet channel exits.

7. The system of claim 1, wherein the free-standing microfluidic pipette includes one or more sensors.

8. The system of claim 1, wherein the free-standing microfluidic pipette includes one or more valves.

9. The system of claim 1, wherein the microfluidic pipette further comprises one or more common channels adapted and configured to be in communication with one or more exits and two or more channels.

10. The system of claim 9, wherein the one or more common channels are adapted and configured to switch, mix, aliquot, or dilute fluids between two or more channel entrances and one or more channel exits.

11. The system of claim 1, wherein the channels are parallel to a plane defined by a bottom surface of the microfluidic pipette, and a distance from one or more exits to said plane is between about 0.001 and about 2 times the height of the one or more exits.

12. The system of claim 1, wherein the exits are separated from each other by a distance between about 0.5 and about 2 times a largest cross-sectional dimension of one or more outlet channel exits.

13. The system of claim 1, wherein the free-standing microfluidic pipette further includes a fluid switching point adapted and configured to be in communication with the outlet channel, the fluid switching point adapted and configured to switch between a plurality of fluids.

14. The system of claim 1, wherein the exits are arranged in a side-by-side arrangement in which an outlet channel exit is positioned between two inlet channel exits.

15. A method of solution exchange comprising:
providing the system of claim 1;
positioning the free-standing microfluidic pipette adjacent to an object of interest in an open volume; and
utilizing the controller to control fluid flows through the channels to generate the localized recirculating fluid flow path outside the pipette and adjacent to the object of interest in an open volume, wherein the liquid leaving the microfluidic pipette through at least one outlet channel exit contacts the object of interest before circulating back and being withdrawn into the at least two inlet channel exits adjacent to the at least one outlet channel exit on the microfluidic pipette.

16. The method of claim 15, further comprising:
applying one or more device to the object of interest, the one or more device selected from the group consisting of: a glass capillary, a patch pipette, an electrode, a microelectrode, an optical fiber, and another device of claim 1.

17. The method of claim 16, further comprising:
applying one or more techniques selected from the group consisting of electroporation and electrophysiological measurement.

18. The method of claim 15, wherein the object of interest is a biological cell and the method further comprises:
transporting cellular responses into the free-standing microfluidic pipette.

19. The method of claim 15, further comprising:
utilizing an optical observation device adapted and configured to facilitate positioning of the exits of the microfluidic pipette adjacent to the object of interest.

20. A system adapted and configured to generate a localized flow circulation zone, the system comprising:
a free-standing microfluidic pipette comprising:
three or more channels including at least two inlet channels and at least one outlet channel with exits separated from each other by an outer surface of the pipette; and
a fluid switching point adapted and configured to be in communication with the at least one outlet channel, the fluid switching point adapted and configured to switch between a plurality of fluids; and
a controller programmed to control fluid flows through each of the three or more channels to generate a localized recirculating fluid flow path outside the pipette, wherein:
(a) liquid leaving the microfluidic pipette through at least one outlet channel exit is withdrawn through at least two inlet channel exits; and
(b):
(i) a ratio of inlet channel exits to outlet channel exits in the microfluidic pipette is greater than 1:1 or
(ii) a total cross-sectional area of the at least two inlet channel exits is greater than a total cross-sectional area of the at least one outlet channel exit.

* * * * *